United States Patent
Leimbach et al.

(10) Patent No.: US 12,402,881 B2
(45) Date of Patent: Sep. 2, 2025

(54) SURGICAL STAPLING DEVICE WITH LOCKOUT SYSTEM FOR PREVENTING ACTUATION IN THE ABSENCE OF AN INSTALLED STAPLE CARTRIDGE

(71) Applicant: Cilag GmbH International, Zug (CH)

(72) Inventors: Richard L. Leimbach, Cincinnati, OH (US); Michael E. Setser, Burlington, KY (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/760,671

(22) Filed: Jul. 1, 2024

(65) Prior Publication Data
US 2024/0350140 A1    Oct. 24, 2024

Related U.S. Application Data

(63) Continuation of application No. 16/230,343, filed on Dec. 21, 2018, now Pat. No. 12,082,814, which is a
(Continued)

(51) Int. Cl.
*A61B 17/072*    (2006.01)
*A61B 17/068*    (2006.01)
(Continued)

(52) U.S. Cl.
CPC .......... *A61B 17/105* (2013.01); *A61B 17/068* (2013.01); *A61B 17/072* (2013.01);
(Continued)

(58) Field of Classification Search
CPC ... A61B 17/105; A61B 17/068; A61B 17/072; A61B 17/07207; A61B 2090/035;
(Continued)

(56) References Cited

U.S. PATENT DOCUMENTS 5,413,267 A    5/1995    Solyntijes et al.
5,462,215 A    10/1995    Viola et al.
(Continued)

FOREIGN PATENT DOCUMENTS

JP    H05-130998 A    5/1993
JP    H05-200038 A    8/1993
(Continued)

OTHER PUBLICATIONS

Extended European Search Report dated Mar. 23, 2020, for Application No. 19219422.3, 8 pages.
(Continued)

*Primary Examiner* — Michelle Lopez
(74) *Attorney, Agent, or Firm* — Frost Brown Todd LLP

(57) ABSTRACT

Surgical stapling instruments having surgical stapling cartridges are disclosed. At least one embodiment includes an end effector that has an elongate channel that is configured to operably support a surgical staple cartridge therein and an anvil that is movably supported on the elongate channel between an open position and closed positions in response to an application of opening and closing motions applied thereto. An anvil lock member cooperates with the anvil to retain the anvil in an open position when a staple cartridge has not been installed in the elongate channel and prevent the anvil from moving to a closed position until the staple cartridge has been seated within the elongate channel. Surgical staple cartridges are configured to move the anvil from an open position to an actuatable position when the cartridge has been installed in the end effector.

20 Claims, 25 Drawing Sheets

Related U.S. Application Data continuation of application No. 14/746,305, filed on Jun. 22, 2015, now Pat. No. 10,166,025, which is a continuation of application No. 13/429,647, filed on Mar. 26, 2012, now Pat. No. 9,078,653.

(51) Int. Cl.
| | | |
|---|---|---|
| *A61B 17/10* | (2006.01) | |
| *A61B 17/00* | (2006.01) | |
| *A61B 17/29* | (2006.01) | |
| *A61B 90/00* | (2016.01) | |

(52) U.S. Cl.
CPC .................. *A61B 17/07207* (2013.01); *A61B 2017/00305* (2013.01); *A61B 2017/00327* (2013.01); *A61B 2017/07214* (2013.01); *A61B 2017/07257* (2013.01); *A61B 2017/07271* (2013.01); *A61B 2017/2923* (2013.01); *A61B 2017/2927* (2013.01); *A61B 2017/2936* (2013.01); *A61B 2090/035* (2016.02)

(58) Field of Classification Search
CPC ........... A61B 2017/00305; A61B 2017/00327; A61B 2017/07214; A61B 2017/07257; A61B 2017/07271; A61B 2017/2923; A61B 2017/2927; A61B 2017/2936
See application file for complete search history.

(56) References Cited

U.S. PATENT DOCUMENTS

| | | | |
|---|---|---|---|
| 5,584,425 | A | 12/1996 | Savage et al. |
| 5,636,780 | A | 6/1997 | Green et al. |
| 5,704,534 | A | 1/1998 | Huitema et al. |
| 5,752,644 | A | 5/1998 | Bolanos et al. |
| 5,762,255 | A | 6/1998 | Chrisman et al. |
| 5,779,130 | A | 7/1998 | Alesi et al. |
| 6,964,363 | B2 | 11/2005 | Wales et al. |
| 7,000,818 | B2 | 2/2006 | Shelton, IV et al. |
| 7,044,352 | B2 | 5/2006 | Shelton, IV et al. |
| 7,044,353 | B2 | 5/2006 | Mastri et al. |
| 7,111,769 | B2 | 9/2006 | Wales et al. |
| 7,143,923 | B2 | 12/2006 | Shelton, IV et al. |
| 7,669,746 | B2 | 3/2010 | Shelton, IV |
| 8,672,209 | B2 | 3/2014 | Crainich |
| 9,078,653 | B2 | 7/2015 | Leimbach et al. |
| 10,166,025 | B2 | 1/2019 | Leimbach et al. |
| 10,639,034 | B2 * | 5/2020 | Harris .............. A61B 17/07207 |
| 10,736,629 | B2 | 8/2020 | Shelton, IV et al. |
| 11,083,458 | B2 | 8/2021 | Harris et al. |
| 12,082,814 | B2 | 9/2024 | Leimbach et al. |
| 2004/0232200 | A1 * | 11/2004 | Shelton, IV ..... A61B 17/07207 227/176.1 |
| 2007/0010838 | A1 * | 1/2007 | Shelton, IV ..... A61B 17/07207 606/157 |
| 2007/0084896 | A1 | 4/2007 | Doll et al. |
| 2008/0023522 | A1 | 1/2008 | Olson et al. |
| 2009/0261143 | A1 | 10/2009 | Wixey et al. |
| 2011/0204120 | A1 | 8/2011 | Crainich |
| 2016/0174969 | A1 | 6/2016 | Kerr et al. |
| 2021/0007743 | A1 | 1/2021 | Cropper et al. |
| 2021/0282770 | A1 * | 9/2021 | Fernandes ........ A61B 17/07207 |
| 2022/0133299 | A1 | 5/2022 | Baxter, III |
| 2022/0133300 | A1 | 5/2022 | Leimbach et al. |

FOREIGN PATENT DOCUMENTS

| | | |
|---|---|---|
| JP | H09-182757 A | 9/1996 |
| JP | H06-503244 A | 11/1997 |
| RU | 2161450 C1 | 1/2001 |
| RU | 61122 U1 | 2/2007 |
| WO | WO 2013/148253 A2 | 10/2013 |

OTHER PUBLICATIONS

Extended European Search Report dated Jul. 23, 2021, for Application No. 21171550.3, 12 pages.
Indian Office Action dated Jun. 16, 2020, for Application No. 7608/DELNP/2014, 5 pages.
International Search Report and Written Opinion dated Jan. 17, 2014, for International Application No. PCT/US2013/031423, 14 pages.
Japanese Notification of Reasons for Refusal dated Mar. 31, 2017, for Application No. 2015-503303, 4 pages.
Russian Office Action dated Mar. 14, 2017, for Application No. 2014143016, 6 pages.
European Examination Report dated Feb. 7, 2019 for Application No. EP 13724428.1, 7 pgs.
Japanese Search Report by Registered Search Organization dated Jan. 18, 2017 for Application No. JP 2015-503303, 18 pgs.

* cited by examiner

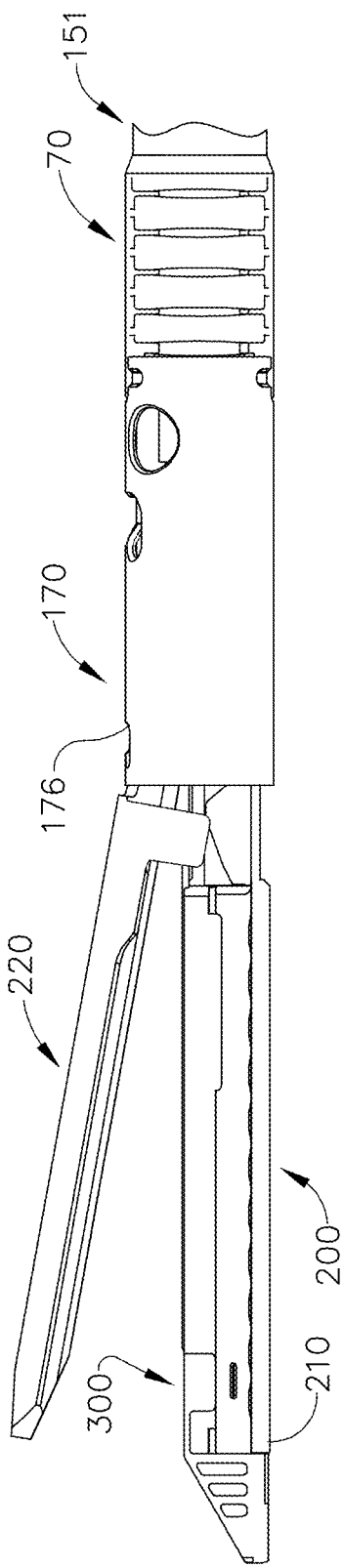
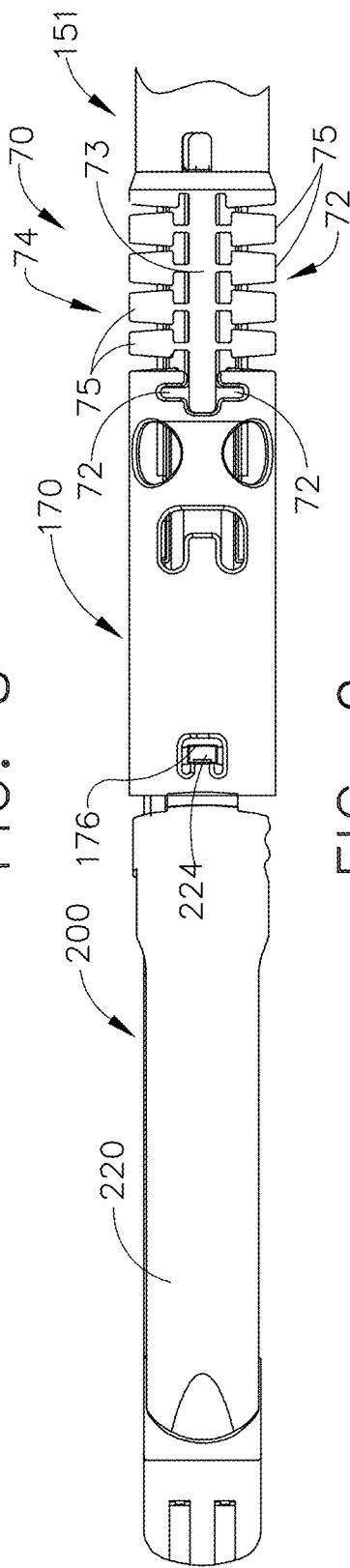
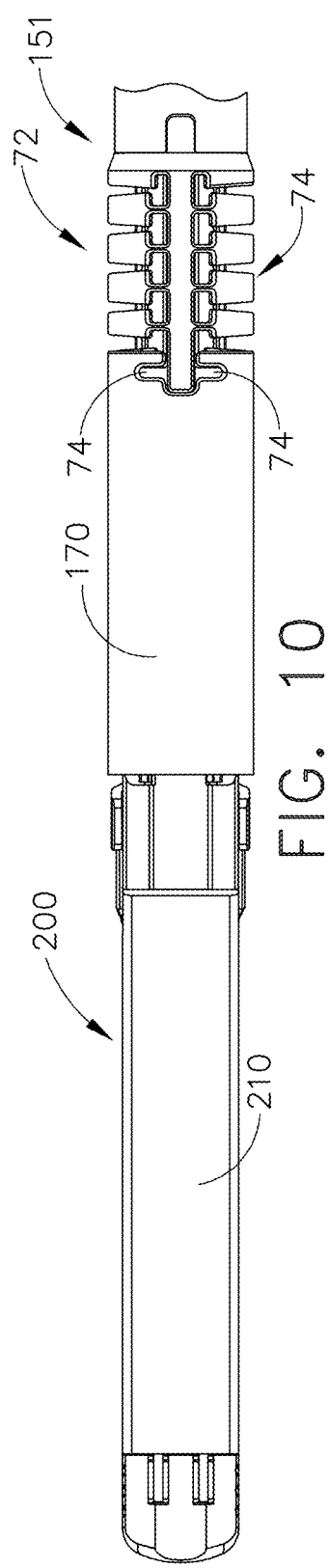
FIG. 8
FIG. 9
FIG. 10

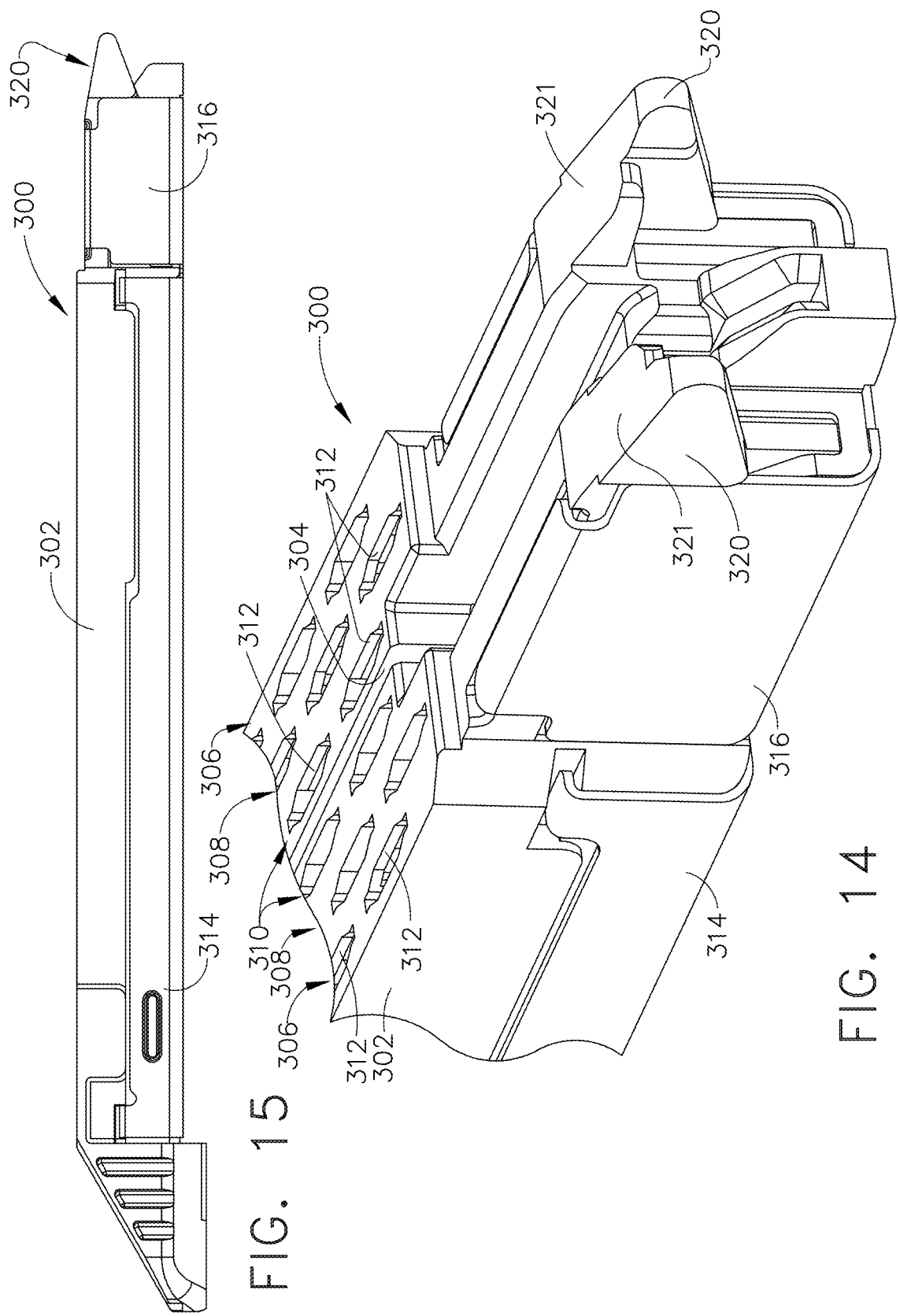

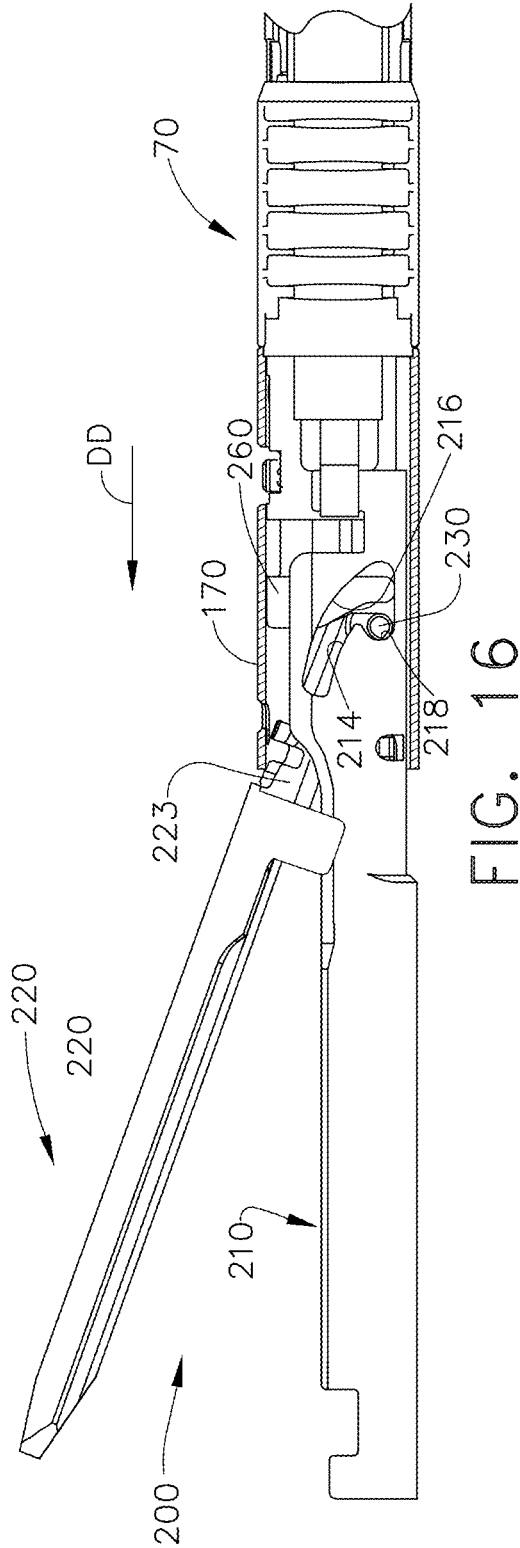
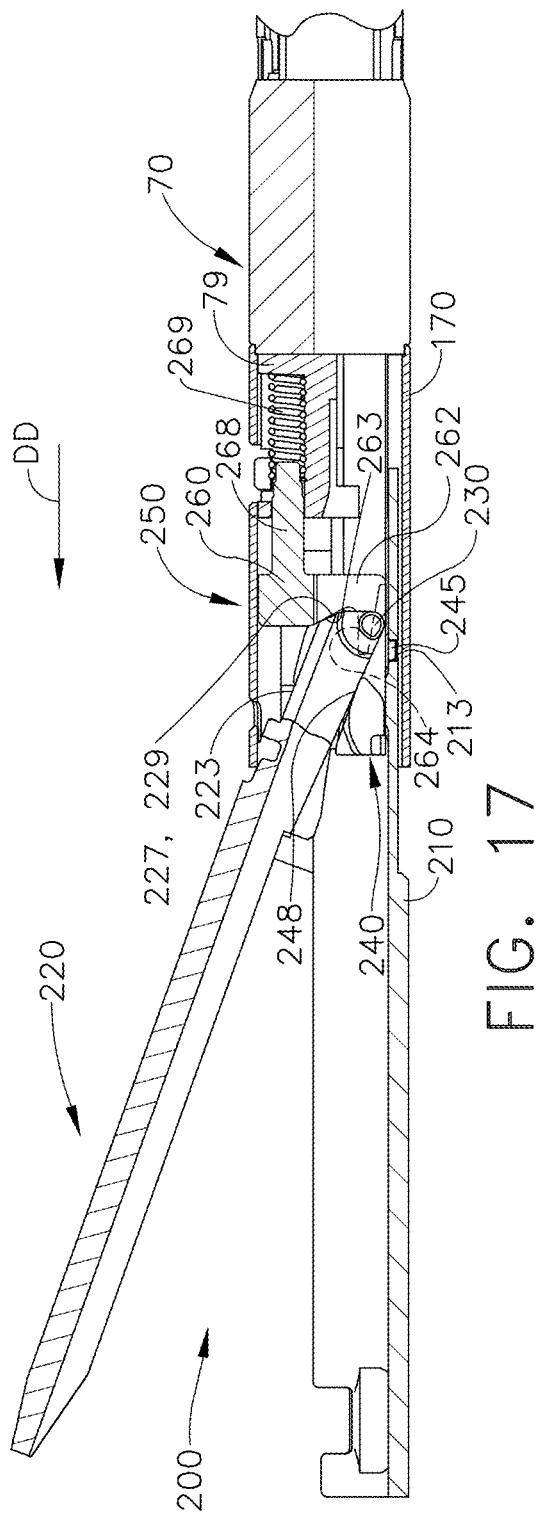

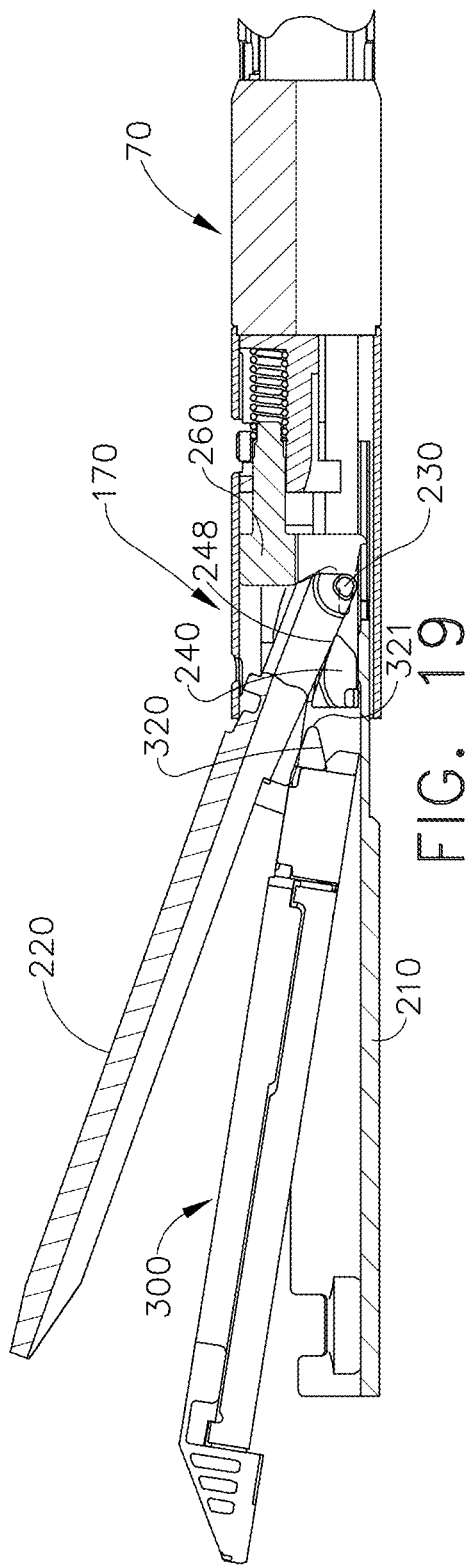
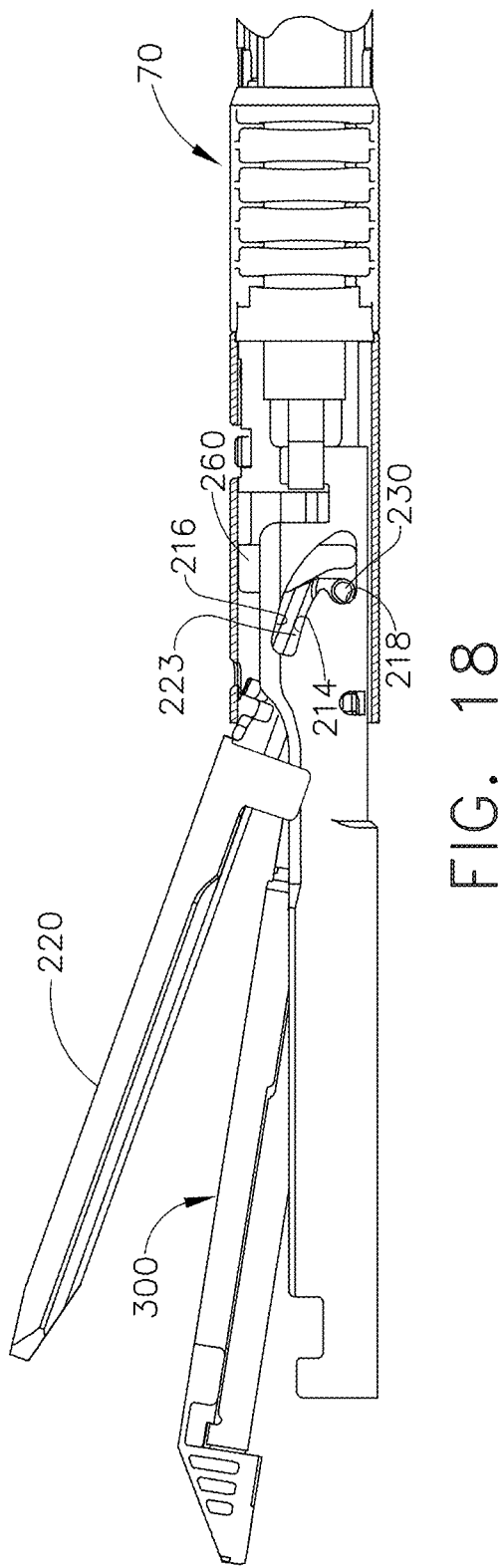

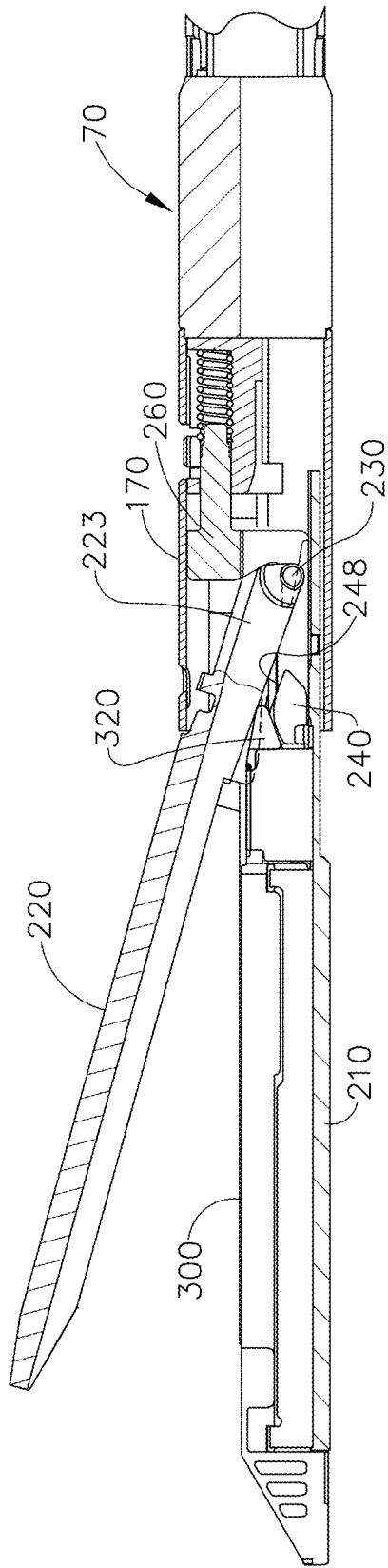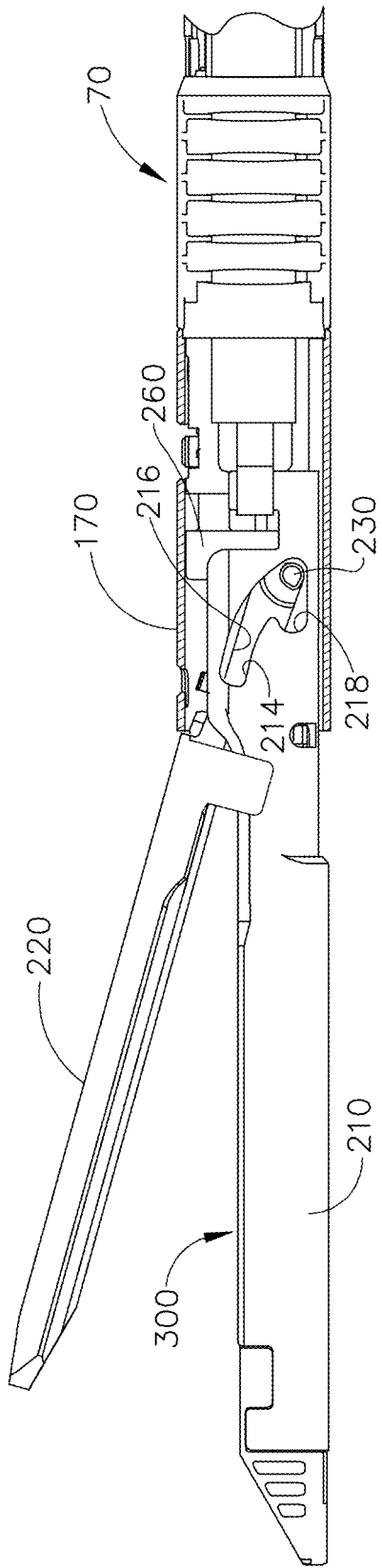

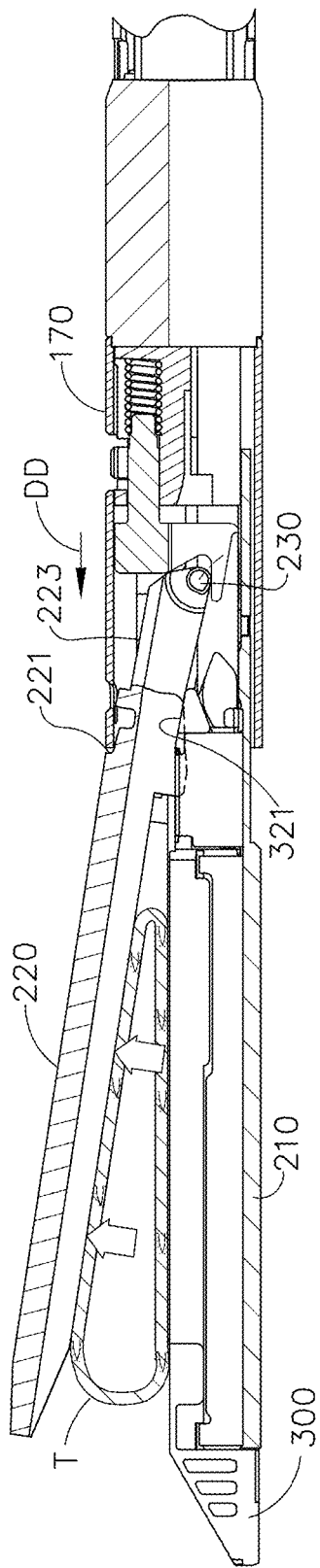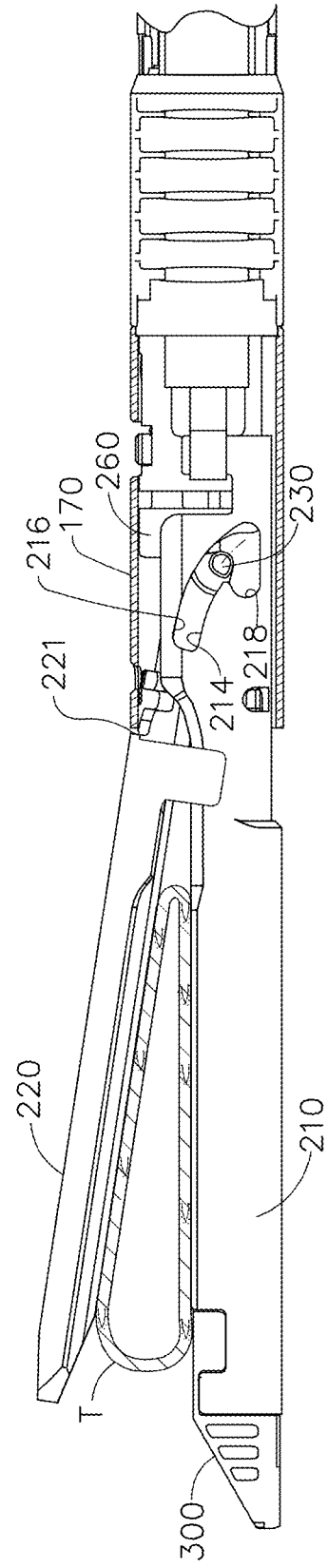

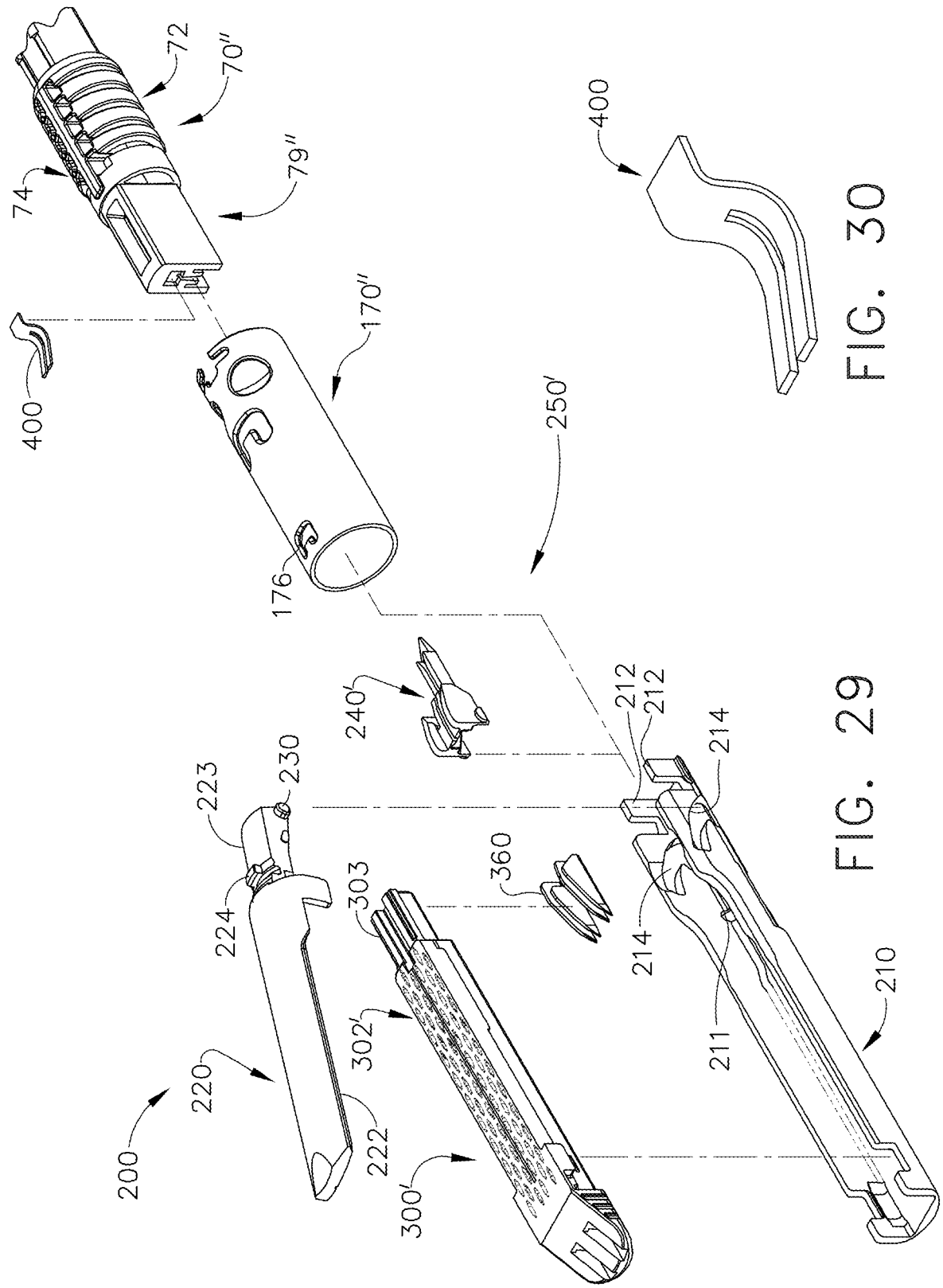

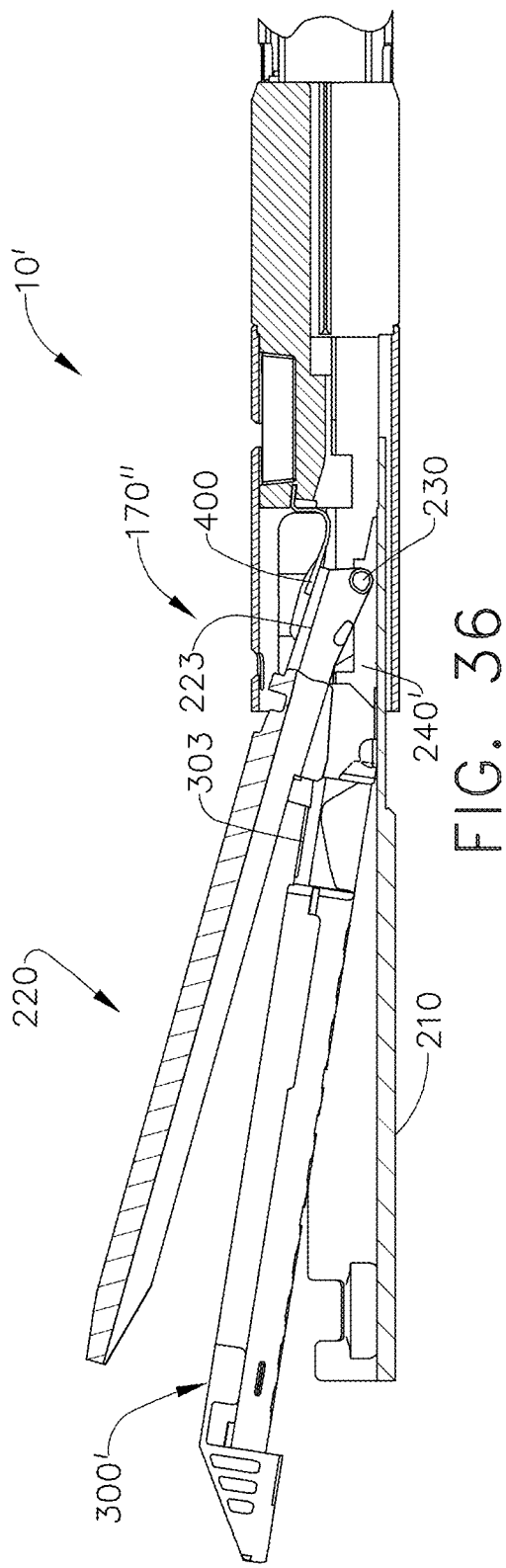
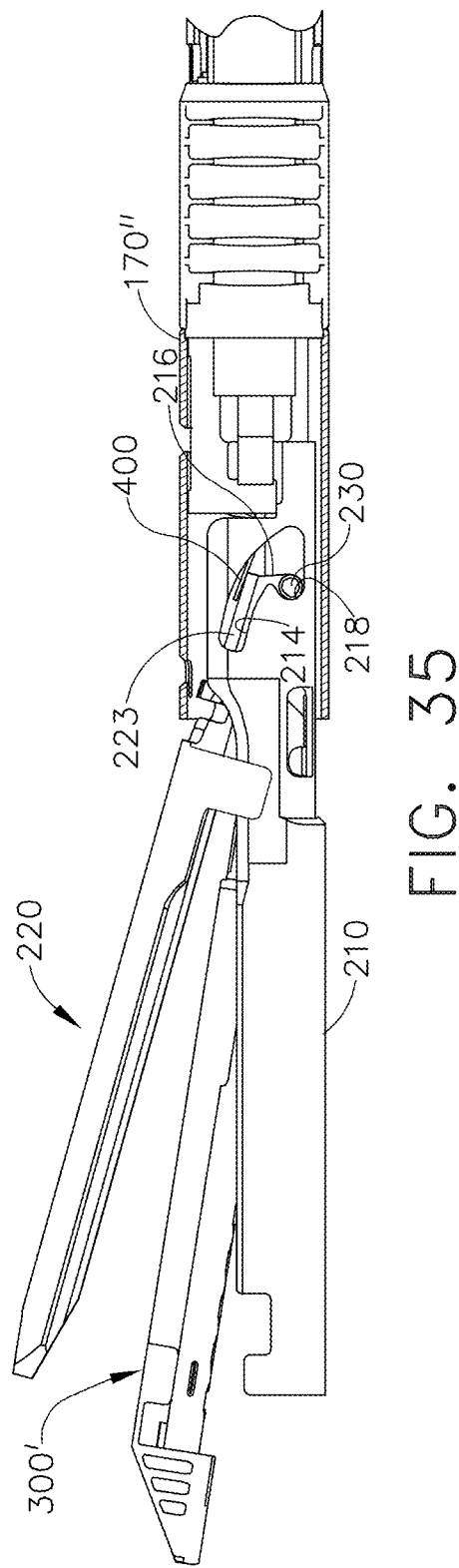

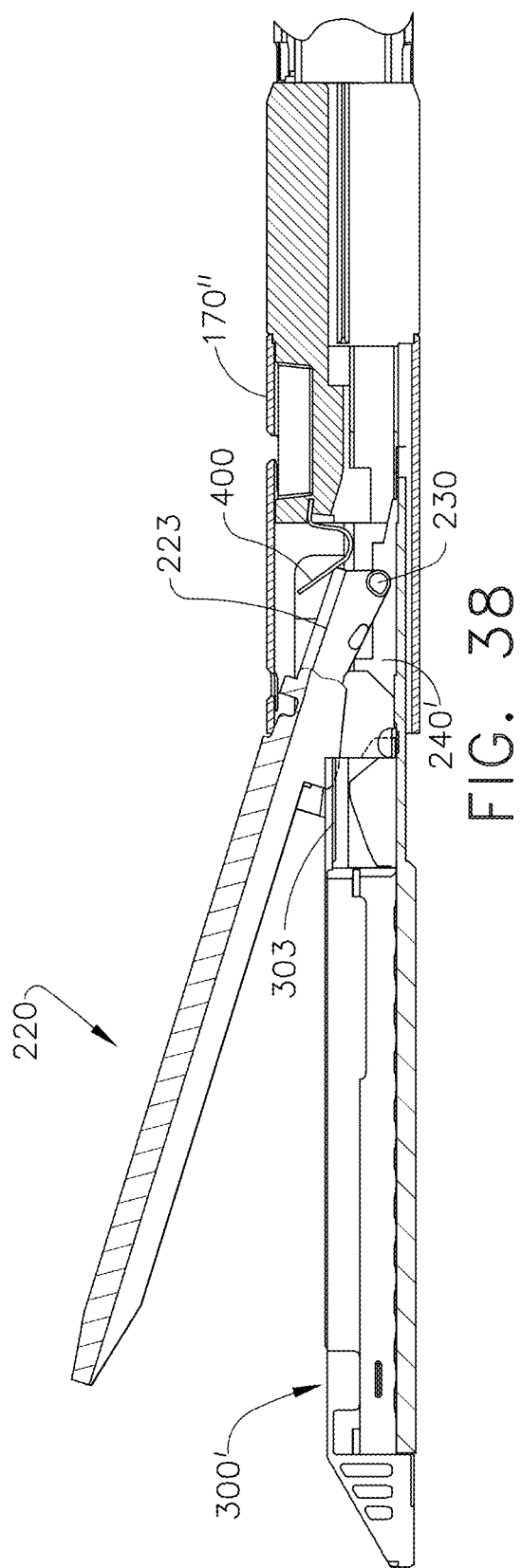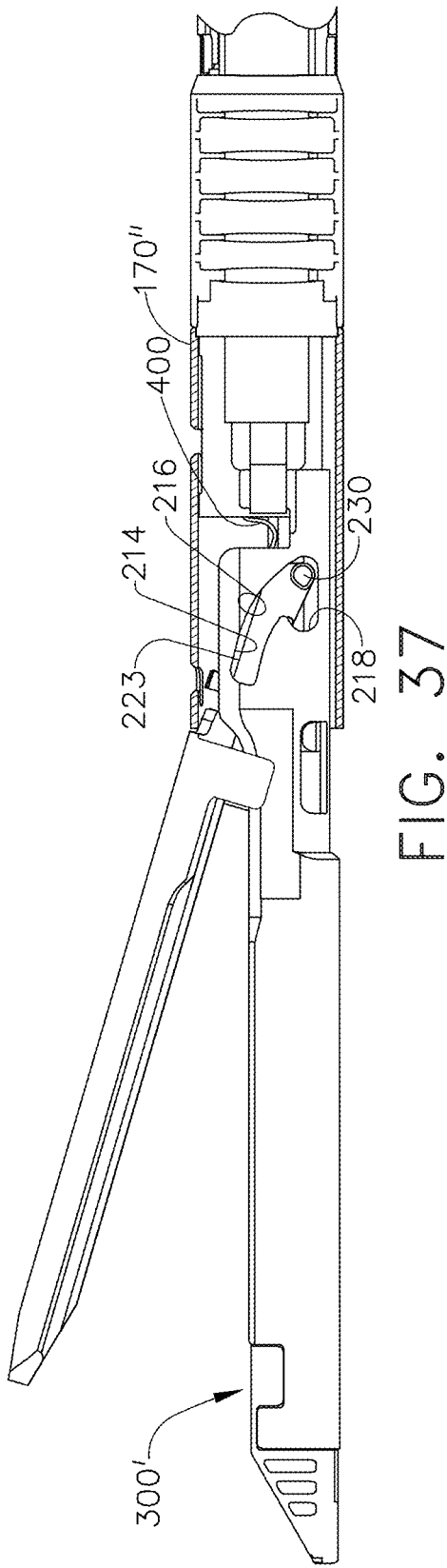

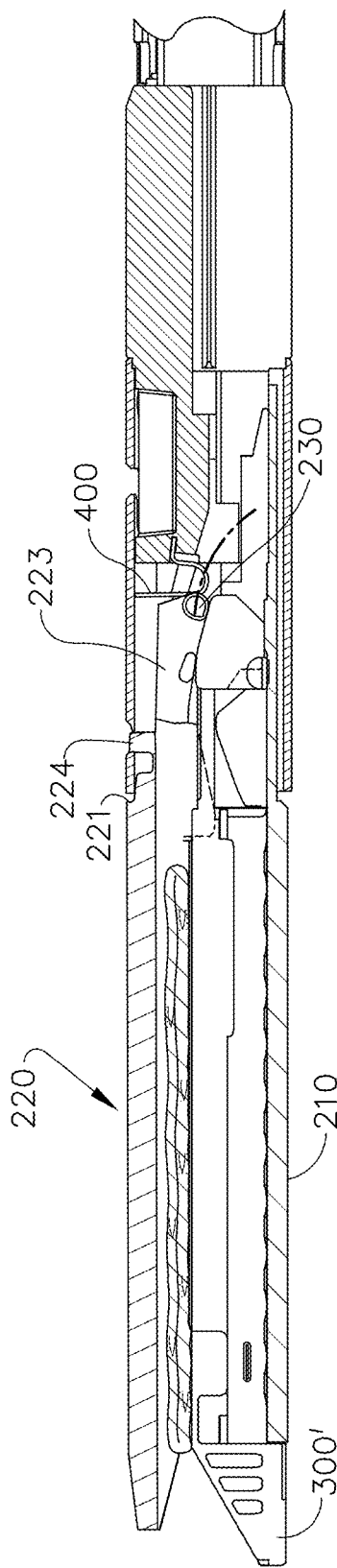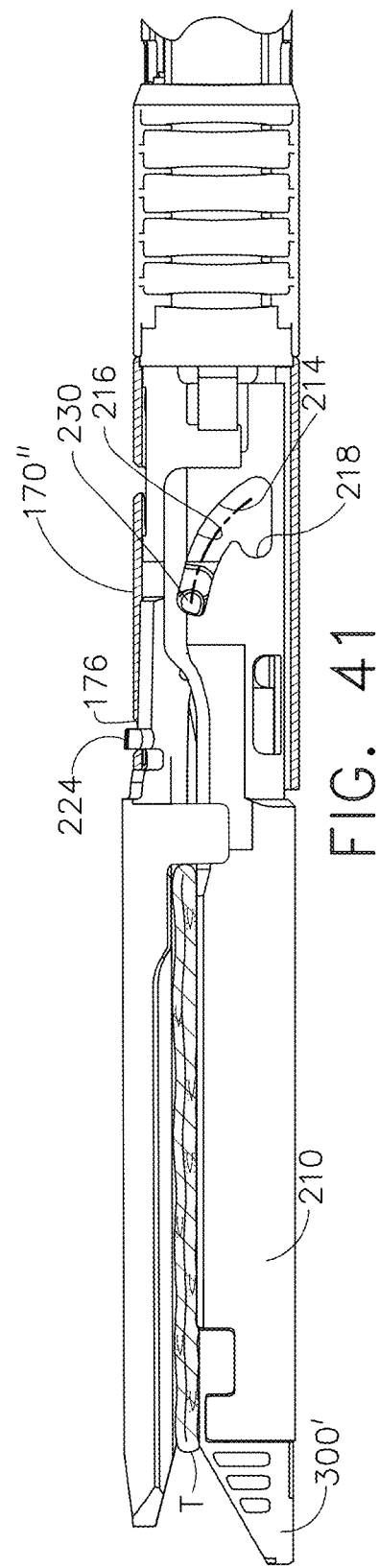

SURGICAL STAPLING DEVICE WITH LOCKOUT SYSTEM FOR PREVENTING ACTUATION IN THE ABSENCE OF AN INSTALLED STAPLE CARTRIDGE

CROSS REFERENCE TO RELATED APPLICATIONS

This application is a continuation application claiming priority under 35 U.S.C. § 120 to U.S. patent application Ser. No. 16/230,343, entitled SURGICAL STAPLING DEVICE WITH LOCKOUT SYSTEM FOR PREVENTING ACTUATION IN THE ABSENCE OF AN INSTALLED STAPLE CARTRIDGE, filed Dec. 21, 2018, published as U.S. Patent Application Publication No. 2019/0192161 on Jun. 27, 2019, issued as U.S. Pat. No. 12,082,814 on Sep. 10, 2024, which is a continuation application claiming priority under 35 U.S.C. § 120 to U.S. patent application Ser. No. 14/746,305, entitled SURGICAL STAPLING DEVICE WITH LOCKOUT SYSTEM FOR PREVENTING ACTUATION IN THE ABSENCE OF AN INSTALLED STAPLE CARTRIDGE, filed Jun. 22, 2015, which issued Jan. 1, 2019 as U.S. Pat. No. 10,166,025, which is a continuation application claiming priority under 35 U.S.C. § 120 to U.S. patent application Ser. No. 13/429,647, entitled SURGICAL STAPLING DEVICE WITH LOCKOUT SYSTEM FOR PREVENTING ACTUATION IN THE ABSENCE OF AN INSTALLED STAPLE CARTRIDGE, filed Mar. 26, 2012, which issued on Jul. 14, 2015 as U.S. Pat. No. 9,078,653, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

SUMMARY

In accordance with at least one general form, there is provided a surgical stapling instrument that includes an end effector that has an elongate channel that is configured to operably support a surgical staple cartridge therein. An anvil is movably supported on the elongate channel between an open position and closed positions in response to an application of opening and closing motions applied thereto. An anvil lock member cooperates with the anvil to retain the anvil in an open position when a staple cartridge has not been installed in the elongate channel and prevents the anvil from moving to a closed position until the staple cartridge has been seated within the elongate channel.

In accordance with at least one other general form, there is provided a surgical stapling instrument that includes a handle and an elongate shaft assembly that is operably coupled to the handle. A closure system is operably supported by the handle for generating closing and opening motions in response to actuation of a closure trigger operably supported by the handle. The instrument further includes an elongate channel that is coupled to the elongate shaft assembly. The instrument also includes an anvil that has an anvil mounting portion that is movably supported on the elongate channel between an open position and closed positions in response to applications of opening and closing motions transmitted thereto through the elongate shaft assembly. An anvil lock member is operably supported by the elongate shaft assembly for movable engagement with the anvil mounting portion. A surgical staple cartridge is configured to be seated within the elongate channel and cooperates with the anvil mounting portion such that when the surgical staple cartridge has not been seated within the elongate channel, the anvil lock member cooperates with the anvil mounting portion to retain the anvil in the open position. In addition, when the surgical staple cartridge is seated within the elongate channel, the staple cartridge moves the anvil mounting portion to a position wherein the anvil may be closed upon application of the closure motions thereto.

In accordance with still another general form, there is provided a surgical staple cartridge for use with a surgical stapling instrument including an end effector with an anvil that is supported in an open position until moved to an actuatable position wherein the anvil is movable to closed positions in response to a closing motion applied thereto by a closure system. In at least one form, the surgical staple cartridge comprises a cartridge body that is sized to be removably seated within a portion of the end effector such that a portion of the cartridge body contacts the anvil to move the anvil from the open position to the actuatable position when seated within the end effector.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 6A is a partial exploded perspective view of another end effector and anvil lock member embodiment;

FIG. 7A is a perspective view of an anvil lock member embodiment of FIG. 6A;

FIG. 8 is a side elevational view of an end effector embodiment in an open position;

FIG. 9 is a top view of the end effector of FIG. 8;

FIG. 10 is a bottom view of the end effector depicted in FIGS. 8 and 9;

FIG. 14 is a perspective view of a proximal end portion of a surgical staple cartridge embodiment;

FIG. 15 is a side elevational view of the surgical staple cartridge embodiment depicted in FIG. 14;

FIG. 16 is a side view of an end effector embodiment prior to seating a staple cartridge in the elongate channel;

FIG. 17 is a cross-sectional view of the end effector depicted in FIG. 16;

FIG. 18 is a side view of an end effector embodiment of FIGS. 16 and 17 with the anvil in the open position and wherein a surgical staple cartridge is being inserted into the elongate channel;

FIG. 19 is a cross-sectional view of the end effector of FIG. 18;

FIG. 20 is a side view of the end effector of FIGS. 16-19 with the staple cartridge embodiment seated within the elongate channel;

FIG. 21 is a cross-sectional view of the end effector of FIG. 20;

FIG. 22 is a side elevational view of the end effector of FIGS. 16-22 clamping tissue;

FIG. 23 is a cross-sectional view of the end effector of FIG. 22;

FIG. 29 is a partial exploded perspective view of an end effector and another anvil lock member embodiment;

FIG. 30 is a perspective view of another anvil lock member embodiment;

FIG. 35 is a side view of an end effector embodiment of FIGS. 33 and 34 with the anvil in the open position and wherein a surgical staple cartridge is being inserted into the elongate channel;

FIG. 36 is a cross-sectional view of the end effector of FIG. 35;

FIG. 37 is a side view of the end effector of FIGS. 33-36 with the staple cartridge embodiment seated within the elongate channel;

FIG. 38 is a cross-sectional view of the end effector of FIG. 37;

FIG. 41 is a side elevational view of the end effector of FIGS. 33-40 in a fully clamped position ready to fire; and FIG. 42 is a cross-sectional view of the end effector of FIG. 41.

DETAILED DESCRIPTION

Figure 1:
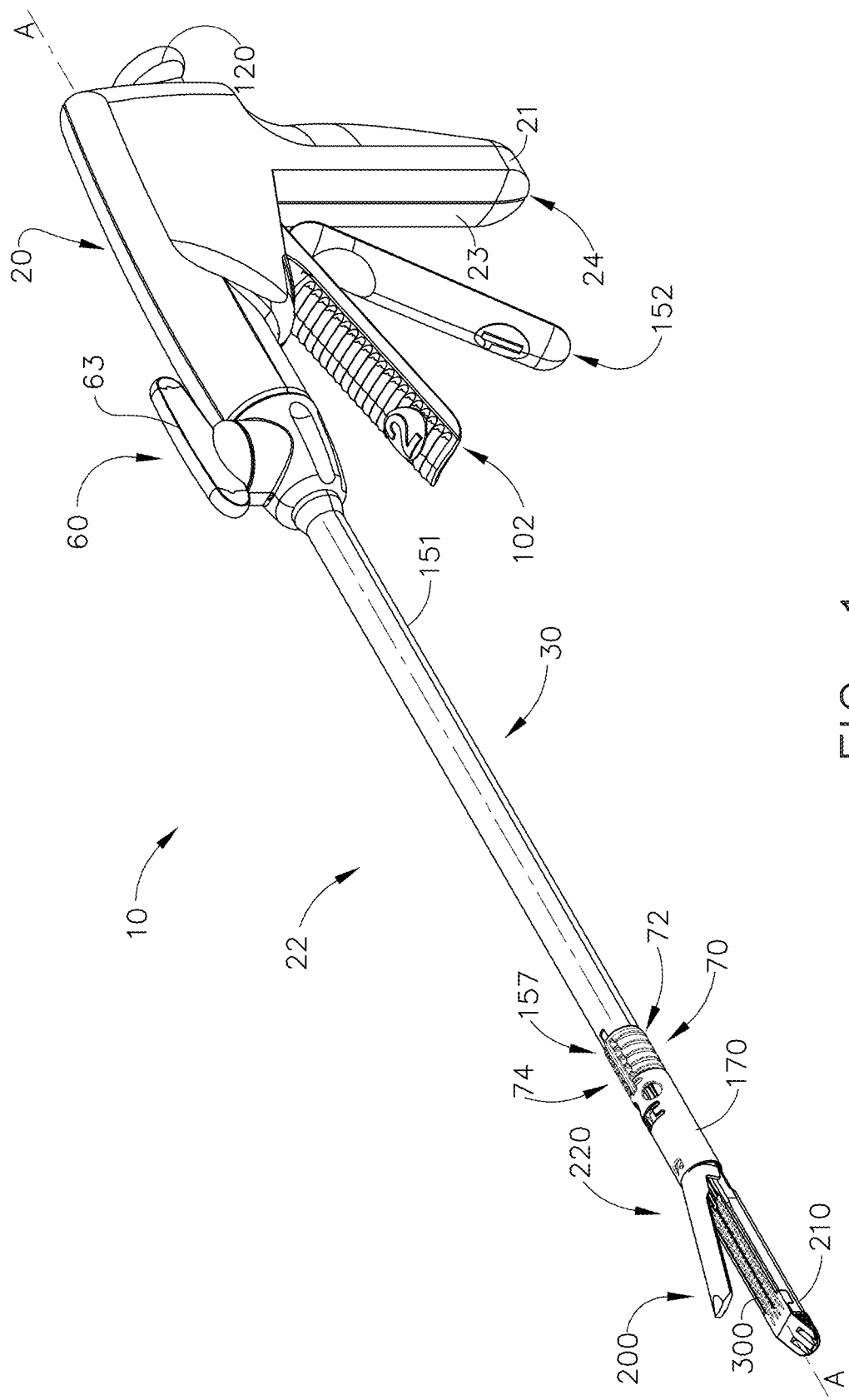
FIG. 1 is a perspective view of a surgical stapling instrument embodiment.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 2:
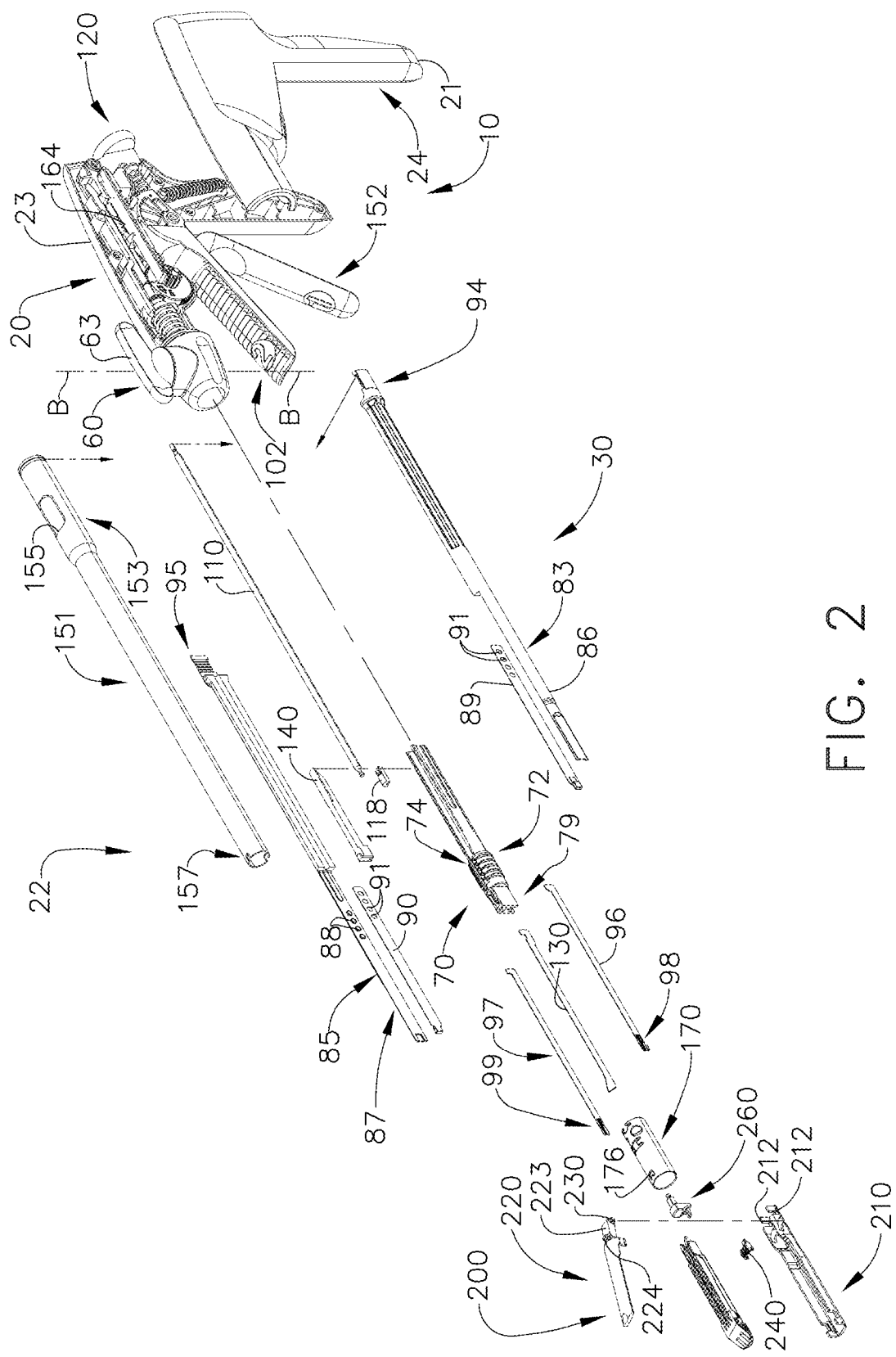
FIG. 2 is an exploded assembly view of the surgical stapling instrument of FIG. 1.

Turning to the Drawings wherein like numerals denote like components throughout the several views, FIGS. 1 and 2 depict a surgical stapling device 10 that is capable of practicing the unique benefits of various embodiments disclosed herein. An exemplary surgical device that has features with which embodiments of the present invention may be effectively employed is disclosed in U.S. Pat. No. 5,704,534, entitled ARTICULATION ASSEMBLY FOR SURGICAL INSTRUMENTS, issued Jun. 6, 1998, the entire disclosure of which is herein incorporated by reference.

Various other exemplary surgical stapling device embodiments are described in greater detail in the following U.S. Patents which are each herein incorporated by reference in their respective entireties: U.S. Pat. No. 6,964,363, entitled SURGICAL STAPLING INSTRUMENT HAVING ARTICULATION JOINT SUPPORT PLATES FOR SUPPORTING A FIRING BAR, issued Nov. 15, 2005; U.S. Pat. No. 7,000,818, entitled SURGICAL STAPLING INSTRUMENT HAVING SEPARATE DISTINCT CLOSING AND FIRING MOTIONS, issued Feb. 21, 2006; U.S. Pat. No. 7,044,352, entitled SURGICAL STAPLING INSTRUMENT HAVING A SINGLE LOCKOUT MECHANISM FOR PREVENTION OF FIRING, issued May 16, 2006; U.S. Pat. No. 7,111,769, entitled SURGICAL INSTRUMENT INCORPORATING AN ARTICULATION MECHANISM HAVING ROTATION ABOUT THE LONGITUDINAL AXIS, issued Sep. 26, 2006; and U.S. Pat. No. 7,143,923, entitled SURGICAL STAPLING INSTRUMENT HAVING A FIRING LOCKOUT FOR AN UNCLOSED ANVIL, issued Dec. 5, 2006.

Referring again to FIGS. 1 and 2, the depicted surgical stapling device 10 includes a handle 20 that is operably connected to an implement portion 22, the latter further comprising an elongate shaft assembly 30 that is operably coupled to an end effector 200. The handle 20 includes a pistol grip 24 toward which a closure trigger 152 is pivotally drawn by the clinician to cause clamping, or closing of an anvil 220 toward an elongate channel 210 of the end effector 200. A firing trigger 102 is farther outboard of the closure trigger 152 and is pivotally drawn by the clinician to cause the stapling and severing of clamped tissue in the end effector 200.

For example, closure trigger 152 is actuated first. Once the clinician is satisfied with the positioning of the end effector 200, the clinician may draw back the closure trigger 152 to its fully closed, locked position proximate to the pistol grip 24. Then, the firing trigger 102 is actuated. The firing trigger 102 springedly returns when the clinician removes pressure. A release button 120 when depressed on the proximal end of the handle 20 releases the locked closure trigger 152.

Articulation System

The depicted embodiment include an articulation assembly 62 that is configured to facilitate articulation of the end effector 200 about the elongate axis A-A of the device 10. Various embodiments, however, may also be effectively employed in connection with non-articulatable surgical stapling devices. As can be seen in FIG. 2, for example, the elongate shaft assembly 30 includes a proximal closure tube segment 151 that is operably supported by a nozzle 60 that is supported on the handle 20. The handle 20 may be formed from two handle cases 21, 23 that operably contain firing and closure systems 100, 150. A proximal end portion 153 of the proximal closure tube segment 151 is rotatably supported by the handle 20 to facilitate its selective rotation about the elongate axis A-A. See FIG. 1. As can also be seen in FIGS. 1 and 2, in at least one embodiment, a distal end portion 157 of the proximal closure tube segment 151 is coupled to a flexible neck assembly 70. The flexible neck assembly 70 has first and second flexible neck portions, 72 and 74, which receive first and second elongate flexible transmission band assemblies 83, 85. The first and second transmission band assemblies 83, 85 have exterior reinforcement band portions 86, 87, respectively, extending distally from the structural portions of the bands. Each exterior reinforcement band portion 86, 87 has a plurality of attachment lugs 88 for securing first and second interior articulation bands 89, 90. See FIG. 2. The transmission band assemblies 83, 85 may be, for example, composed of a plastic, especially a glass fiber-reinforced amorphous polyamide, sold commercially under the trade name Grivory GV-6H by EMS-American Grilon. In contrast, it may be desired that the interior articulation bands 89, 90 of the transmission band assemblies 83, 85 be composed of a metal, advantageously full hard 301 stainless steel or its equivalent. The attachment lugs 88 on the exterior reinforcement band portions 86, 87 of the transmission bands 83, 85 are received into and secured within a plurality of lug holes 91 on the corresponding interior articulation band 89, 90. At the distal end of the first and second interior articulation band assemblies 89, 90 there are first and second connectors 92, 93. The articulation assembly further comprises distal articulation bands 96 and 97 that are configured to hookingly engage the first and second connectors 92, 93, respectively. The articulation bands 96 and 97 have receptacles 98, 99 to couple the bands 96, 97 to the end effector 200 as will be discussed in further detail below.

Figure 3:
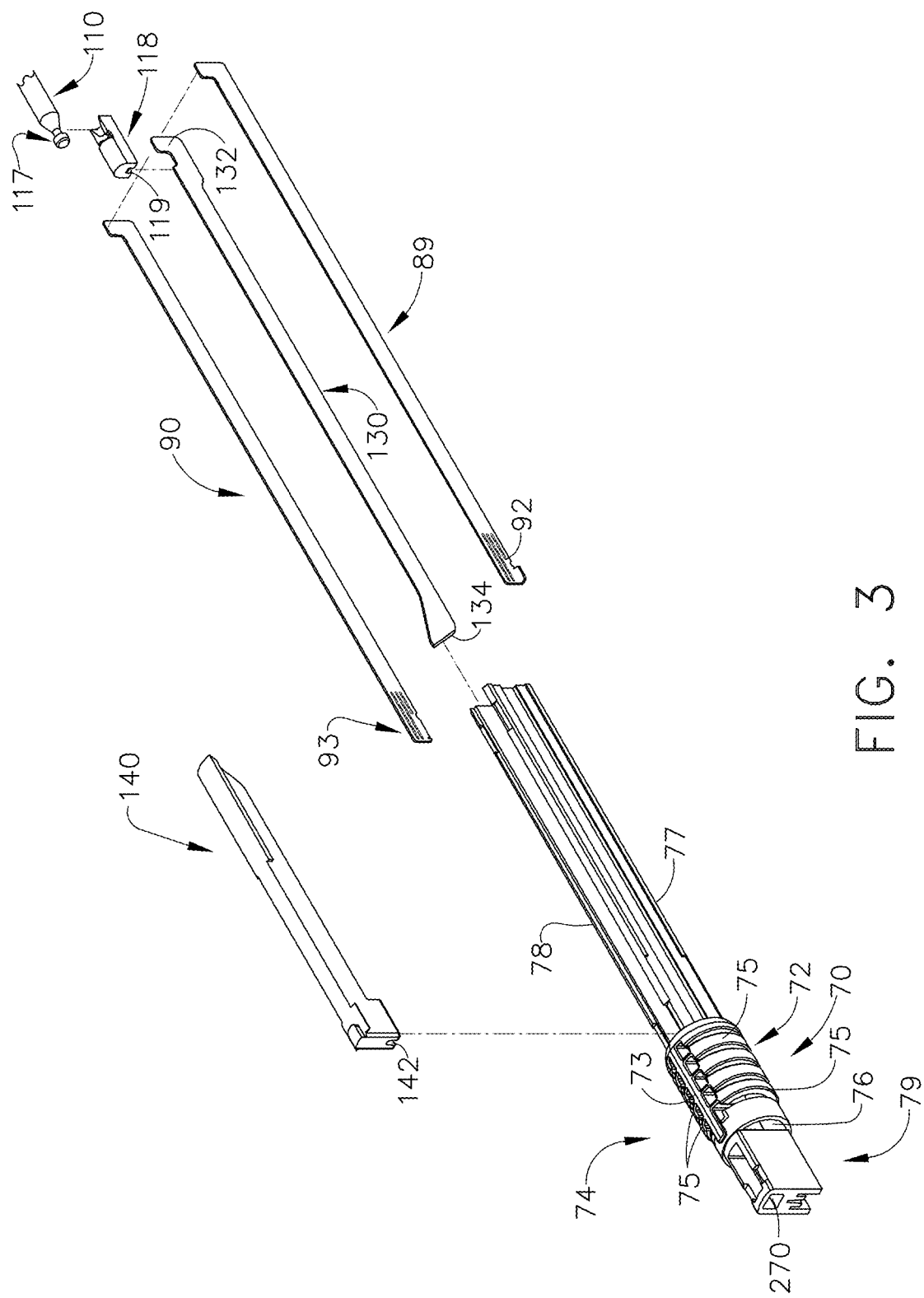
FIG. 3 is an exploded assembly view of a portion of an articulation assembly embodiment.

In at least one form, the flexible neck assembly 70 is preferably composed of a rigid thermoplastic polyurethane sold commercially as ISOPLAST grade 2510 by the Dow Chemical Company. As can be seen in FIG. 3, the flexible neck assembly 70 has first and second flexible neck portions 72, 74. These neck portions 72, 74 are separated by a central longitudinal rib 73. See FIG. 6. The neck portions 72, 74 each have a plurality of neck ribs 75 configured essentially as semi-circular disks. The flexible neck portions 72, 74 together generally form a cylindrical configuration. A side slot 76 extends through each of the neck ribs 75 to provide a passage through the first and second flexible neck portions 72, 74 for receiving the interior articulation bands 89, 90 and exterior reinforcement band portions 86, 87 of the flexible band assemblies 83, 85. In a similar fashion, the central longitudinal rib 73 separating the first and second flexible neck portions 72, 74 has a central longitudinal slot for providing a passage to receive the stapler actuating members. Extending proximally from the first and second flexible neck portions 72, 74 are first and second support guide surfaces 77, 78 for supporting the reciprocating movement of the interior articulation bands 89, 90 and the exterior reinforcement portions 86, 87 of the flexible transmission band assemblies 83, 85. Extending from the distal end of the flexible neck portions 72, 74 is a channel guide 79 for guiding the movement of the stapler actuating members into a staple cartridge 300 of the end effector 200 as will be further discussed below.

In at least one form, when the first and second transmission band assemblies 83, 85 are brought into contact with each other during assembly of the instrument 10, they form an elongate cylinder which has a longitudinal cavity through it that is concentrically positioned between the band assemblies 83, 85 for the passage of a firing rod 110. The proximal ends of the first and second bands have first and second gear racks 94, 95 which, as will be discussed below, meshingly engage an articulation assembly 62.

Figure 4:
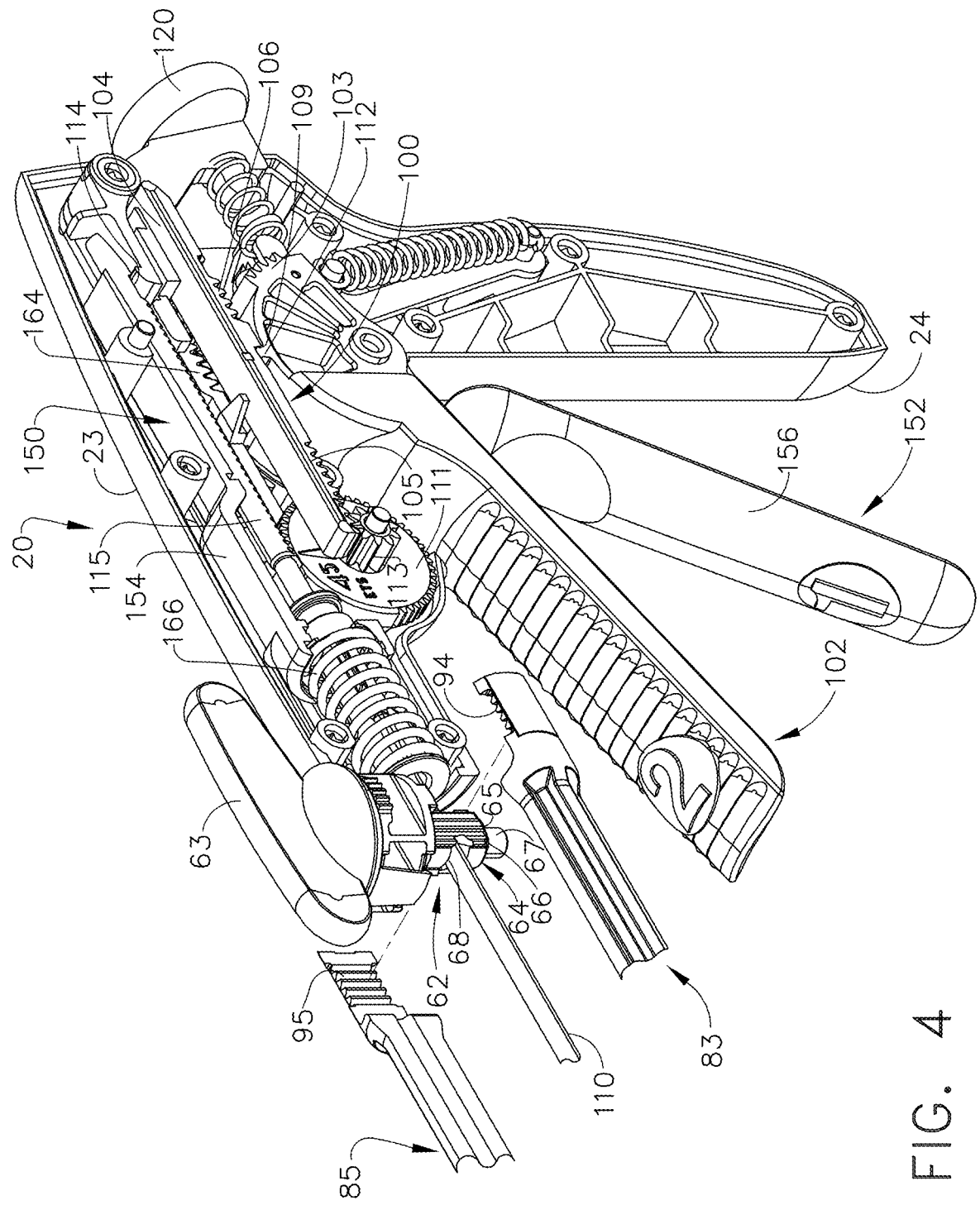
FIG. 4 is a partial exploded perspective view of a portion of the handle.
Figure 5:
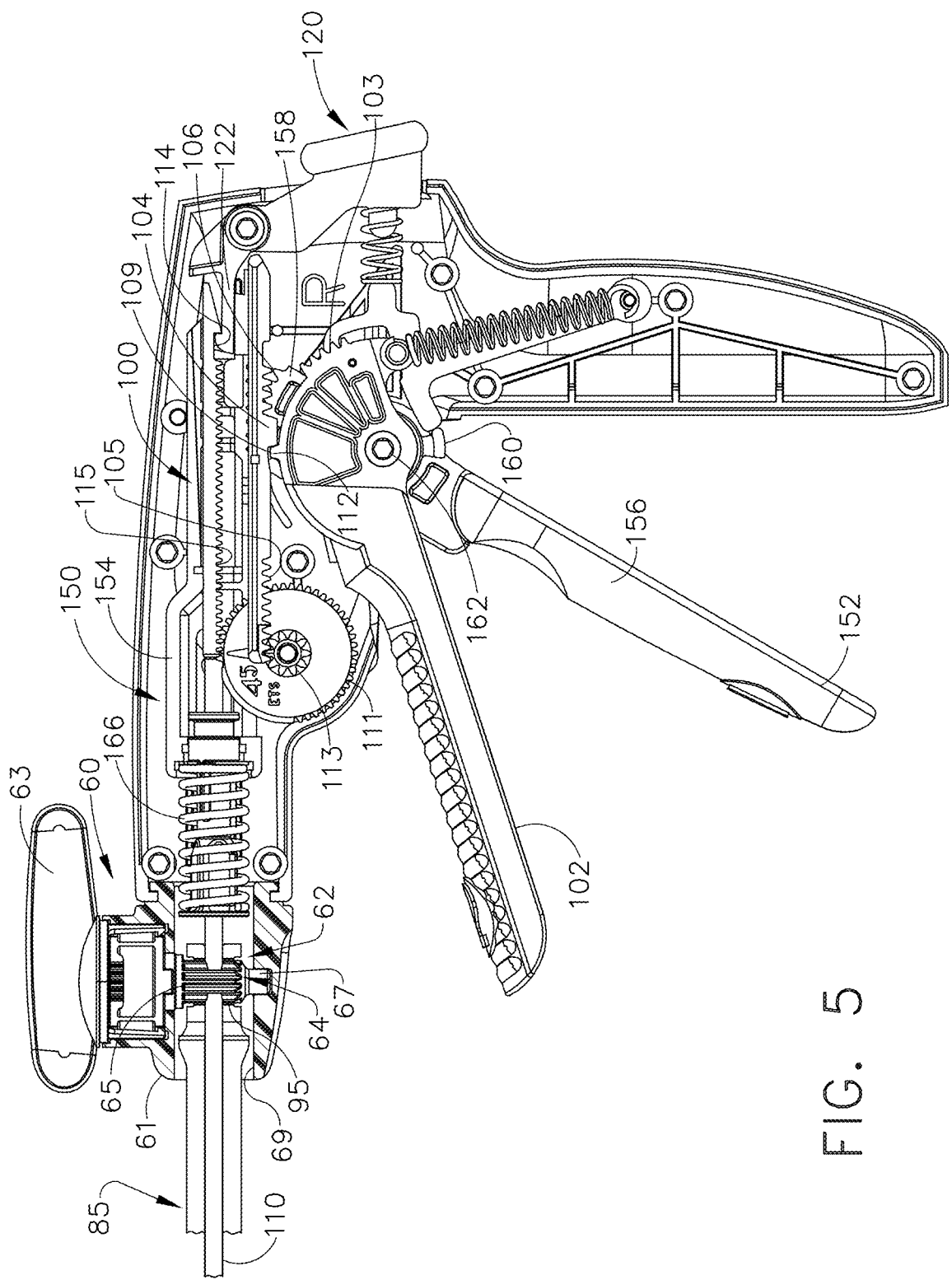
FIG. 5 is a side view of the handle with a handle case removed.

Upon rotation of the articulation assembly 62, one of the first and second flexible transmission band assemblies is moved forwardly and the other band assembly is moved rearwardly. In response to the reciprocating movement of the band assemblies 83, 85 within the first and second flexible neck portions 72, 74 of the flexible neck assembly 70, the flexible neck assembly 70 bends to provide articulation. As can be seen in FIG. 5, an articulation assembly 62 includes an actuator 63, an articulation body 64 and the nozzle 60. Rotational movement of the actuator 63 causes corresponding rotation of the articulation body 64 within the nozzle 60. The first and second elongate transmission band assemblies 83, 85, consequently reciprocate axially in opposite directions parallel to the longitudinal axis A-A of the endoscopic shaft 30 of the stapling device 10 to cause the remote articulation of the end effector 200 through the flexible neck assembly 70. The articulation body 64 further includes a drive gear 65 thereon. As can be seen in FIG. 4, the drive gear 65 has a flared opening 66 through it, and a lower pivot 67. Within the flared opening 66 of the drive gear 65, there is a firing rod orifice 68 for receiving the firing rod 110 enabling the firing of staples into the clamped tissue in response to pivotal rotation of the firing trigger 102. The drive gear 65 is supported for meshing engagement with the first and second drive racks 94, 95 on the flexible elongate transmission band assemblies 83, 85 to effect the desired reciprocating movement of the band assemblies 83, 85.

As can be seen in FIG. 5, the nozzle 60 of the articulation assembly 62 has a nozzle body 61. The nozzle body 61 has an axial bore 69 extending through it for receiving the drive gear 65 of the articulation body 64. The bore 69 provides a continuous opening axially from the frame into the elongate endoscopic shaft 30 and therefore the firing rod 110 and other operative components of the stapling device 10 can communicate with the end effector 200. Further details relating to the articulation assembly 62 may be found in U.S. Pat. No. 5,704,534, which has been previously herein incorporated by reference.

Closure System

Figure 24:
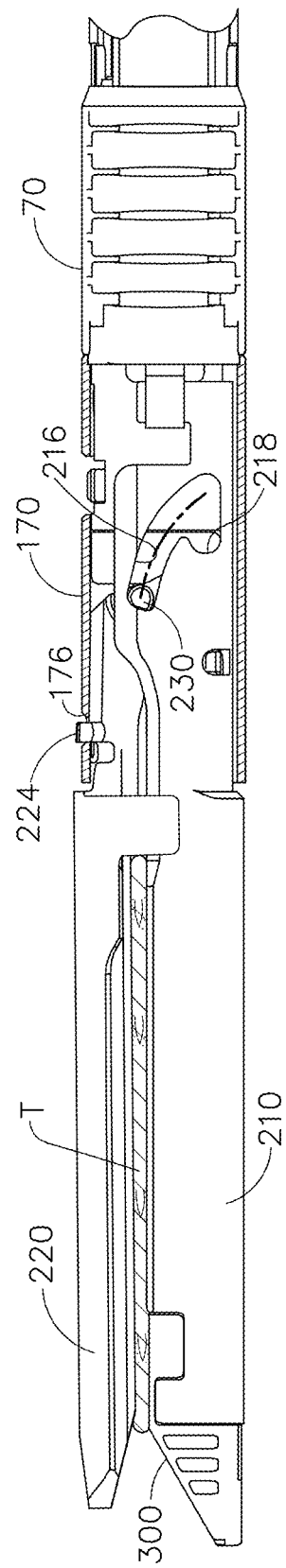
FIG. 24 is a side elevational view of the end effector of FIGS. 16-23 in a fully clamped position ready to fire.
Figure 25:
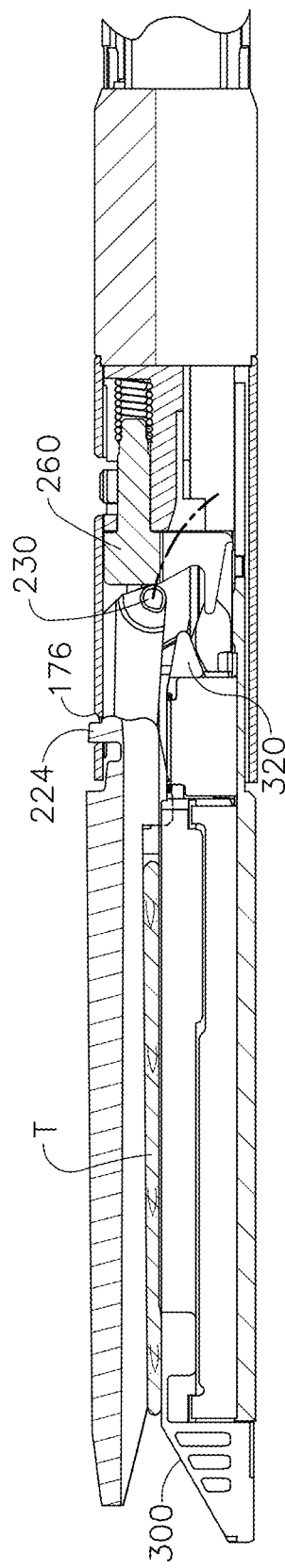
FIG. 25 is a cross-sectional view of the end effector of FIG. 24.

As will be discussed in further detail below, the end effector 200 comprises an elongate channel 210 that is configured to operably receive a surgical staple cartridge 300. An anvil 220 is movably supported relative to the elongate channel 210 and is moved from an open position (FIGS. 16 and 17) to closed positions wherein tissue may be cut and stapled (FIGS. 24 and 25). The movement of the anvil 220 between open and closed positions is at least partially controlled by a closure system, generally designated as 150, which, as indicated above, is controlled by the closure trigger 152. The closure system 150 includes the proximal closure tube segment 151 that operably houses the articulation band assemblies 83, 85 in the manner discussed above and which is non-movably coupled to the flexible neck assembly 70.

In various forms, the proximal closure tube segment 151 includes a proximal end portion 153 that axially extends through the bore 69 in the nozzle 60. The proximal closure tube segment 151 has elongate axial slots 155 therethrough to permit the articulation body 64 to extend therethrough. See FIG. 2. The slots 155 enable the articulation body 64 to rotate about articulation axis B-B relative to the proximal closure tube segment 151 while facilitating the axial movement of the proximal closure tube segment 151 along axis A-A relative to articulation body 64. The transmission bands 83, 85 function as a frame upon which the proximal closure tube segment 151 can axially move. The proximal end 153 of the proximal closure tube segment 151 is rotatably coupled to a closure yoke 154 that is supported within the handle 20 for reciprocating motion therein. See FIGS. 4 and 5.

The closure trigger 152 has a handle section 156, a gear segment section 158 and an intermediate section 160. See FIG. 5. A bore extends through the intermediate section 160. A cylindrical support member 162 extending from the second handle housing 23 passes through the bore for pivotably mounting the closure trigger 152 on the handle portion 20. A proximal end 98 of the closure yoke 154 has a gear rack 164 that is engaged by the gear segment section 158 of the closure trigger 152. When the closure trigger 152 is moved toward the pistol grip 24 of the handle portion 20, the closure yoke 154 and, hence, the proximal closure tube segment 151 move distally, compressing a spring 166 that biases the closure yoke 152 proximally.

In at least one form, the closure system 150 further includes a distal closure tube segment 170 that is non-movably coupled to the channel guide portion 79 of the flex neck assembly 70 by attachment tabs 72, 74. See FIGS. 9 and 10. The distal closure tube segment 170 has an opening 176 therein that is adapted to interface with an upstanding tab 224 formed on the anvil 220 as will be discussed in further detail below. Thus, axial movement of the proximal closure tube segment 151 results in axial movement of the flex neck assembly 70, as well as the distal closure tube segment 170. For example, distal movement of the proximal closure tube segment 151 effects pivotal translation movement of the anvil 220 distally and toward the elongate channel 210 of the end effector 200 and proximal movement effects opening of the anvil 220 as will be discussed in further detail below.

Firing System

In at least one form, the surgical instrument 10 further includes a firing system, generally designated as 100, for applying firing motions to the firing rod 110 in response to actuation of the firing trigger 102. In at least one form, the firing system 100 further includes a drive member 104 that has first and second gear racks 105, 106 thereon. A first notch 109 is provided on the drive member 105 intermediate the first and second gear racks 105, 106. During return movement of the firing trigger 102, a tooth 112 on the firing trigger 102 engages with the first notch 109 for returning the drive member 104 to its initial position after staple firing. A second notch 114 is located at a proximal end of the firing rod 110 for locking the firing rod 110 to an upper latch arm 122 of the release button 120 in its unfired position. The firing system 150 further includes first and second integral pinion gears 111, 113. The first integral pinion gear 111 is engaged with a drive rack 115 provided on the firing rod 110. The second integral pinion gear 113 is engaged with the first gear rack 105 on the drive member 104. The first integral pinion gear 111 has a first diameter and the second integral pinion gear 113 has a second diameter which is smaller than the first diameter.

In various embodiments, the firing trigger 102 is provided with a gear segment section 103. The gear segment section 103 engages the second gear rack 106 on the drive member 104 such that motion of the firing trigger 102 causes the drive member 104 to move back and forth between first and second drive positions. In order to prevent staple firing before tissue clamping has occurred, the upper latch arm 122 on the release button 120 is engaged with the second notch 114 on the drive rack 115 such that the firing rod 110 is locked in its proximal-most position. When the upper latch arm 122 falls into a recess in the closure yoke, the upper latch arm 122 disengages with the second notch 114 to permit distal movement of the firing rod 110. Because the first gear rack 105 on the drive member 104 and the drive rack 115 on the firing rod 110 are engaged, movement of the firing trigger 102 causes the firing rod 110 to reciprocate between a first reciprocating position and a second reciprocating position. Further details concerning various aspects of the firing system 150 may be gleaned from reference to U.S. Pat. No. 7,000,818 which has been herein incorporated by reference in its entirety.

As can be seen in FIG. 3, various embodiments, the distal end 117 of the firing rod 110 is rotatably received within a firing bar mounting yoke 118. The firing bar mounting yoke 118 has a slot 119 for hookingly receiving a hook 132 formed on a proximal end of a knife bar 130. In addition, as shown in FIG. 3, a support bar 140 is supported for axial movement between the first and second support guide surfaces 77, 78 of the flex neck assembly 70. The support bar 140 has a slot 142 that is configured to permit the knife bar 130 to slidably pass therethrough. The metal knife bar 130 has a tissue cutting edge 134 formed on its distal end and is configured to operably interface with a wedge sled operably supported within a surgical staple cartridge 300.

End Effector

Figure 6:
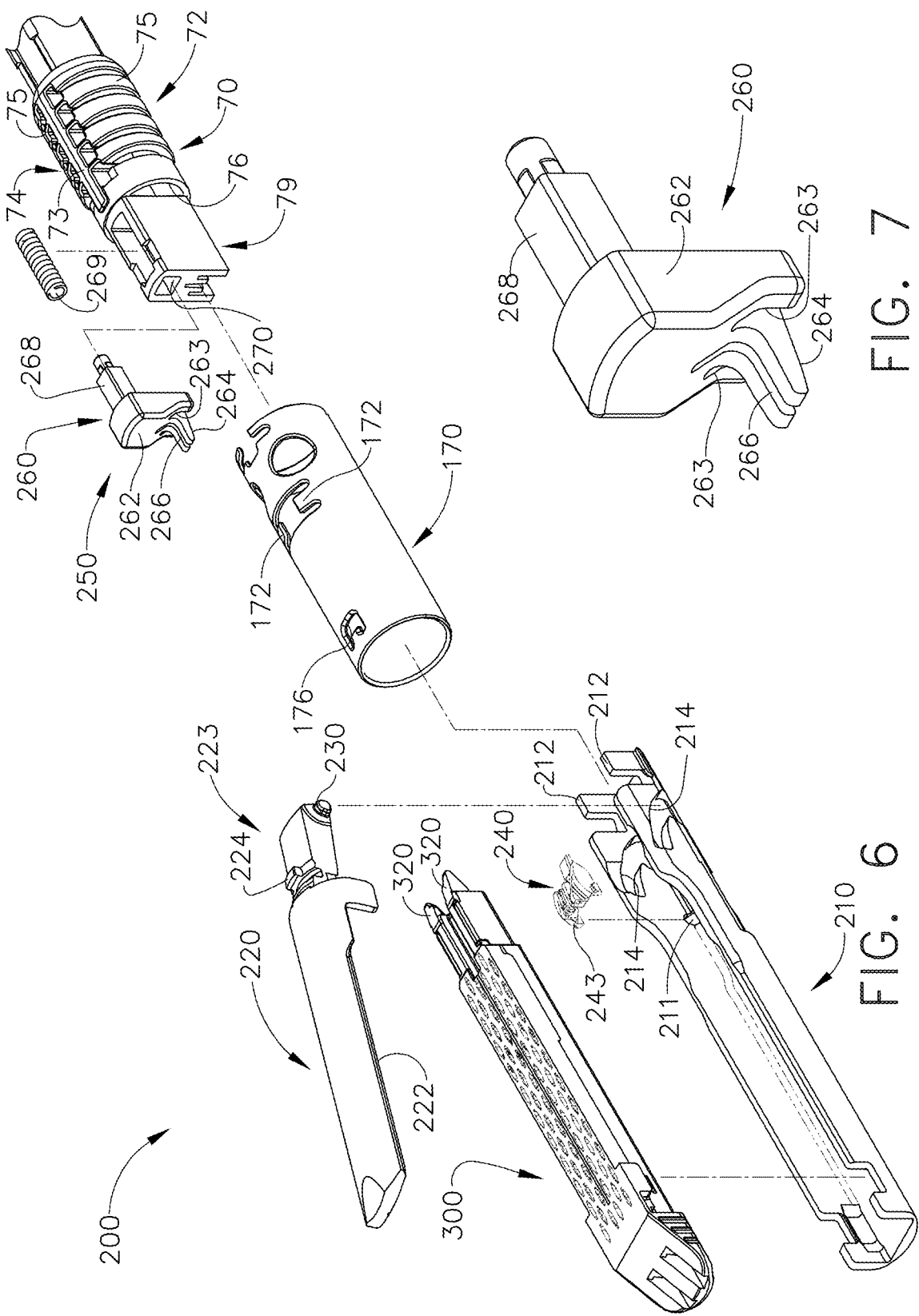
FIG. 6 is a partial exploded perspective view of an end effector and anvil lock embodiment.
Figure 11:
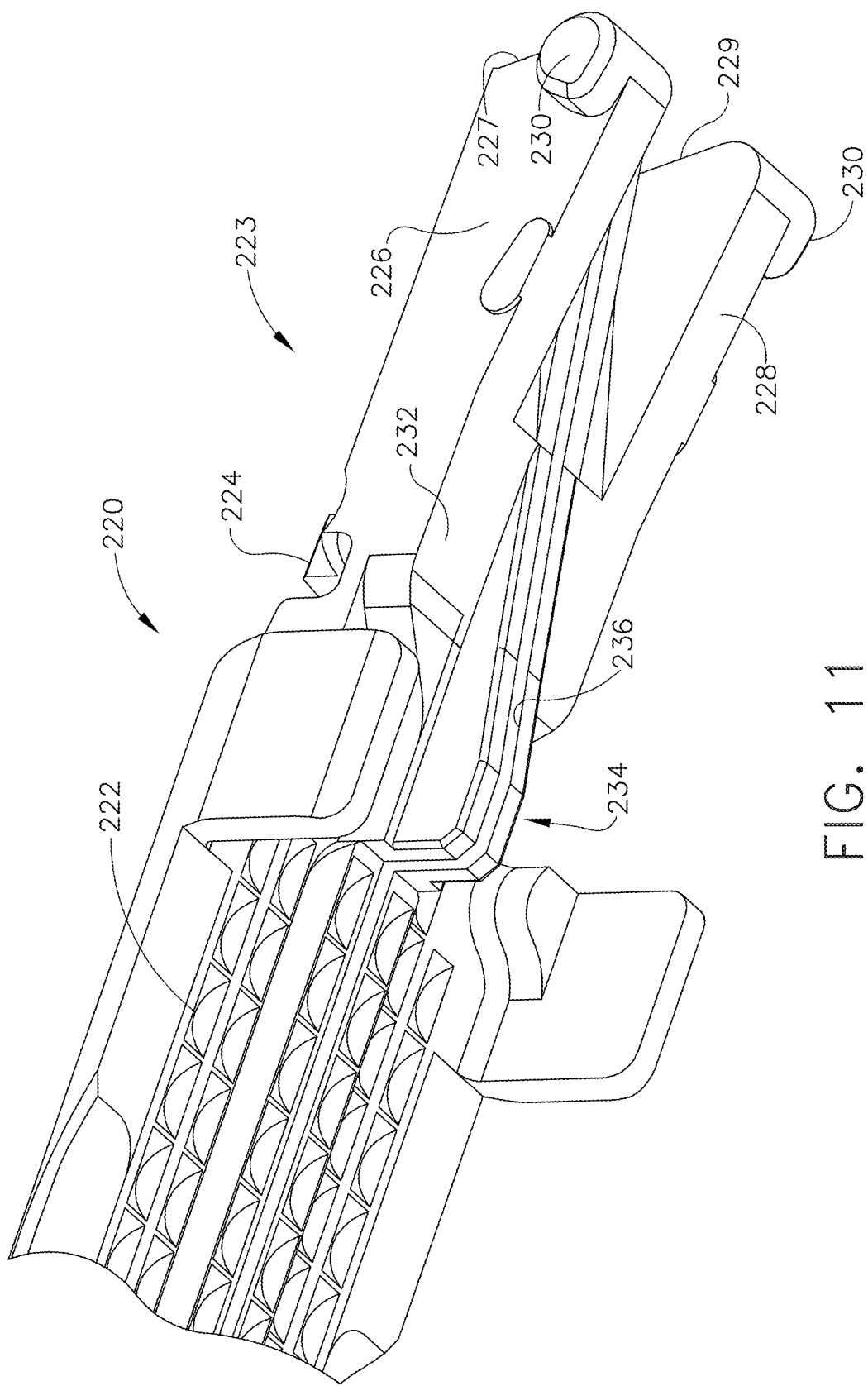
FIG. 11 is a partial bottom perspective view of an anvil embodiment.

As discussed above, in at least one form, an end effector 200 includes an elongate channel 210 that is configured to operably support a surgical staple cartridge 300 therein. As shown in FIGS. 2 and 6, the elongate channel 210 has a proximal end portion that includes two spaced mounting tabs 212 that are configured to be engaged by the hooks 998, 99 on the distal ends of the articulation bands 96, 97. Thus, the reciprocating motions of the articulation bands 96, 97 cause the elongate channel 210 to articulate relative to the flex neck assembly 70. As further indicated above, the end effector 200 also includes an anvil 220. In at least one form, the anvil 220 is fabricated from, for example, 416 Stainless Steel Hardened and Tempered RC35 Min (or similar material) and has a staple-forming undersurface 222 thereon that is configured for confronting engagement with the staple cartridge 300 when mounted in the elongate channel 210. The anvil 220 is formed with a proximally extending mounting portion 223 that includes two trunnion walls 226, 228 that each has a trunnion 30 protruding therefrom. See FIG. 11. In addition, formed on the underside 232 of the mounting portion 223 is a downwardly protruding pivot tab 234 that has a slot 236 extending therethrough that is configured to receive and support the knife bar 130 as it is axially advanced through the end effector 200 during cutting and stapling. In addition, the anvil opening tab 224 is formed on the mounting portion 223 such that it can operably interface with the opening 176 in the distal closure tube segment 170 as will be further discussed below. As can be seen in FIGS. 16-25, the anvil trunnions 230 are configured to be movably received in corresponding trunnion slots 214 formed in the proximal end of the elongate channel 210. Each trunnion slot 214 has an arcuate segment 216 that communicates with a locking notch 218.

Figure 13:
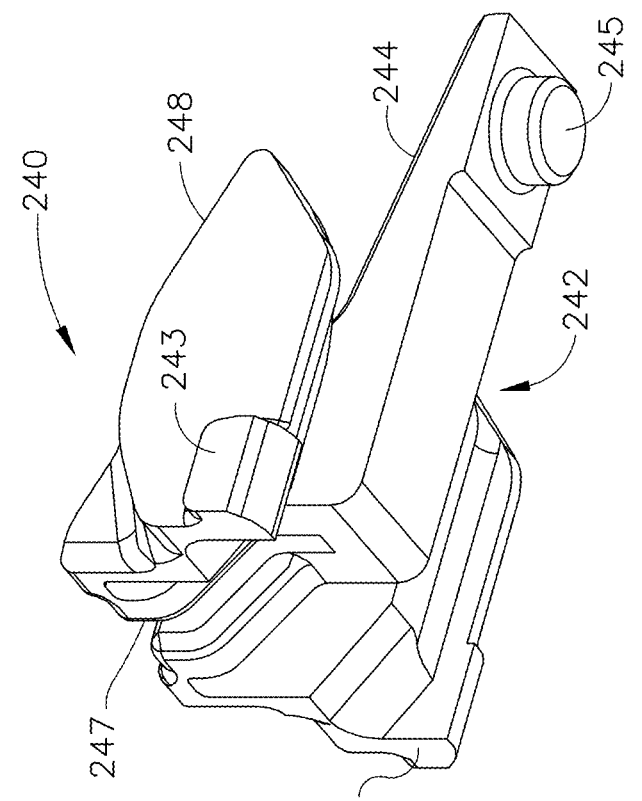
FIG. 13 is a bottom perspective view of the pivot mount embodiment of FIG. 12.
Figure 12:
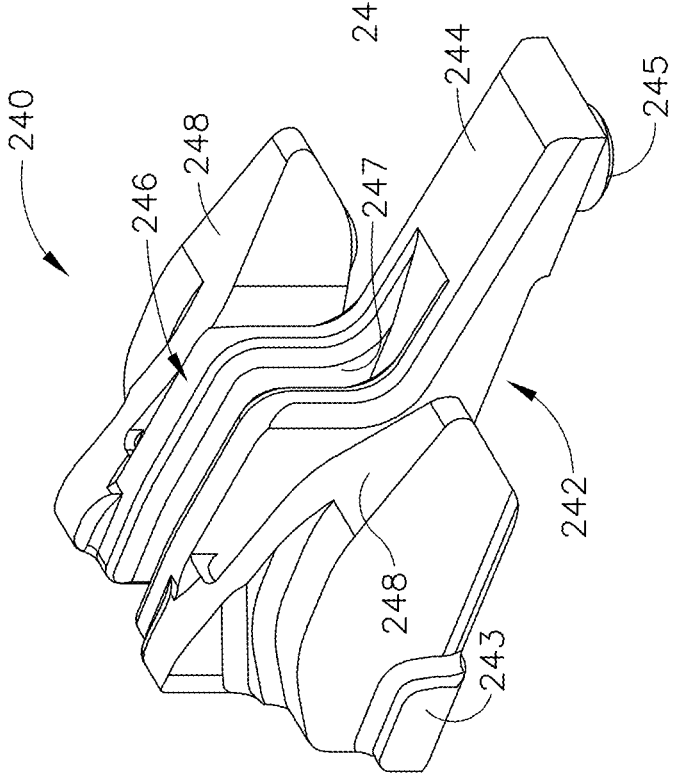
FIG. 12 is a perspective view of a pivot mount embodiment.

To facilitate pivotal travel of the anvil mounting portion 223 relative to the elongate channel 210, various embodiments include a pivot mount 240. As can be in FIGS. 12 and 13, one form of a pivot mount 240 has a body portion 242 that is configured to be attached to the elongate channel 210. For example, the body portion 242 may be formed with two opposed attachment tabs 243 that are configured to retainingly engage tab openings 211 (FIG. 6) formed in the elongate channel 210. In addition, the pivot mount 240 has a proximally extending foot portion 244 that has a retainer lug 245 protruding therefrom that is configured to be received in a corresponding opening 211 in the elongate channel 210. See FIG. 17. The pivot mount 240 may be fabricated from, for example, Vectra A435 Liquid Crystal Polymer-natural or similar materials. As can be further seen in FIGS. 12 and 13, the body portion 242 has an upstanding central portion 246 that has a slot 247 extending therethrough for axially receiving the knife bar 130. The central portion 246 provides lateral support to the knife bar 130 as it is driven through tissue clamped within the end effector 200. Various embodiments of the pivot mount 240 further include rocker surfaces 248 formed on each side of the central portion 246 for pivotally receiving the trunnion walls 226, 228 of the anvil 220 thereon.

Anvil Lockout System

Figure 7:
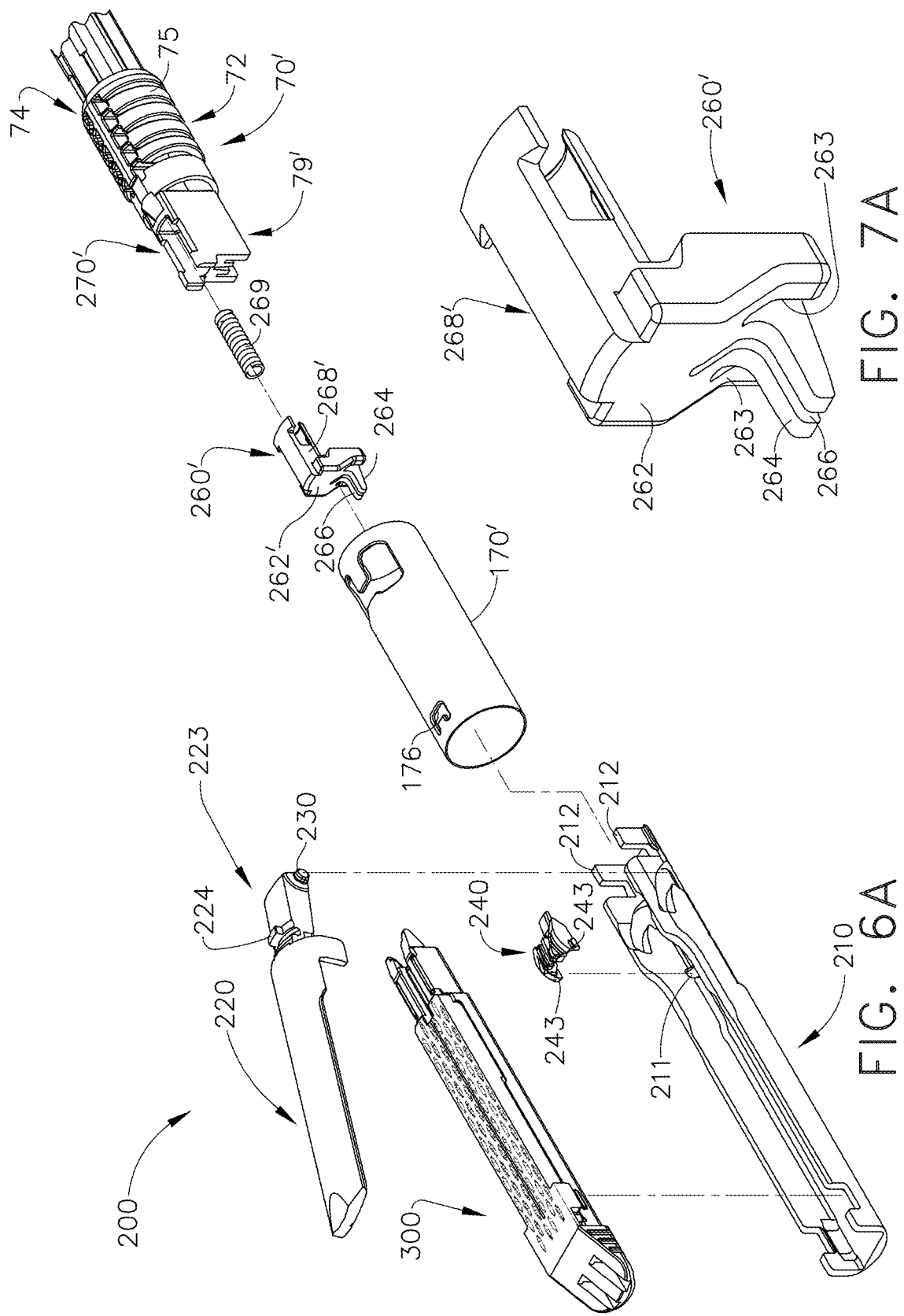
FIG. 7 is a perspective view of an anvil lock member embodiment.

Various embodiments include a unique and novel anvil lockout system 250 that prevents closure of the anvil 220 when a staple cartridge 300 has not been properly installed in the elongate channel 210. Referring to FIGS. 6 and 7, for example, an embodiment of an anvil lockout system 250 includes a movable anvil lock member 260 that is movable in response to contact by a portion or portions of a staple cartridge 300 as will be discussed in further detail below. In at least one form, the anvil lock member 260 comprises a body portion 262 that has a distally protruding central support tab 264 formed thereon. A slot 266 extends through body portion 262 and the central support tab 264 to enable the knife bar 130 to pass therethrough. The body portion 262 further includes proximally extending mounting bar 268 that is configured to be slidably received within a corresponding mounting opening 270 in the channel guide 79 of the flex neck assembly 70. In addition, a biasing member in the form of, for example, a coil spring 269 is supported within the opening 270 to bias the anvil lock member 260 in the distal direction "DD". See FIG. 16. When the anvil 220 is mounted to the elongate channel 210, the trunnions 230 are received within their corresponding trunnion slots 214 in the elongate channel 210, the central support tab 264 of the anvil lock member 260 is received between the trunnion walls 226, 228 to further provide support to the anvil 220. The body portion 262 of the anvil lock member 260 is further formed with two cam surfaces 263 configured to engage the proximal end surfaces 227, 229 of the trunnion walls 226, 228. See FIGS. 6 and 7. Various embodiments of the anvil lock member may be fabricated from, for example, Vectra A435 Liquid Crystal Polymer-natural or similar materials.

FIGS. 6A and 7A illustrate an alternative anvil lock member 260' that is movable in response to contact by a portion or portions of a staple cartridge 300. In at least one form, the anvil lock member 260' comprises a body portion 262 that has a distally protruding central support tab 264 formed thereon. A slot 266 extends through body portion 262 and the central support tab 264 to enable the knife bar 130 to pass therethrough. The body portion 262 further includes proximally extending mounting bar 268' that is configured to be slidably and retainably received within a corresponding mounting opening 270' in the channel guide 79' of the flex neck assembly 70'. In addition, a biasing member in the form of, for example, a coil spring 269 is supported within the opening 270' to bias the anvil lock member 260' in the distal direction "DD". The anvil lock member 260' otherwise operates in the same manner as anvil lock member 260. When the anvil 220 is mounted to the elongate channel 210, the trunnions 230 are received within their corresponding trunnion slots 214 in the elongate channel 210, the central support tab 264 of the anvil lock member 260' is received between the trunnion walls 226, 228 to further provide support to the anvil 220. The body portion 262 of the anvil lock member 260 is further formed with two cam surfaces 263 configured to engage the proximal end surfaces 227, 229 of the trunnion walls 226, 228. The distal closure tube segment 170' operates in the same manner as the distal closure tube segment 170 described above.

Surgical Staple Cartridge

Various embodiments include a unique and novel surgical staple cartridge 300 that is configured to interact with the anvil lockout system 250 when installed in the elongate channel 210. As can be seen in FIGS. 14 and 15, in at least one form, the surgical staple cartridge 300 includes a cartridge body 302 that may be fabricated from, for example, Vectra A435, 20% PTFE/15% GF-natural. The cartridge body 302 is sized and shaped to be received within the elongate channel 210. In at least one form, the cartridge body 302 is configured to be seated in the elongate channel 210 such that is removably retained therein. The cartridge body 302 may be formed with a centrally disposed slot 304 therein for receiving the knife bar 130. On each side of the slot 304, there is provided rows 306, 308, 310 of staple openings 312 that are configured to support a surgical staple therein. In the depicted embodiment, three rows 306, 308, 310 are provided on each side of the slot 304. The surgical staples may be supported on staple drivers that are movably supported within the staple openings 312. Also supported within the staple cartridge body 302 is a wedge sled that is configured for axial movement through the cartridge body 302 when contacted by the cutting bar. The wedge sled is configured with wedge-shaped driving members that contact the staple drivers and drive the drivers and their corresponding staples toward the closed anvil as the wedge sled is driven distally through the cartridge body 302. Examples of staple driver arrangements and wedge sled arrangements that may be employed are described in further detail in U.S. Pat. No. 7,669,746, the entire disclosure which is herein incorporated by reference. In various embodiments, to facilitate installation of the wedge sled and drivers in the cartridge body 302, metal cartridge pans 314, 316 may be attached to the cartridge body 302 as shown in FIGS. 14 and 15. The cartridge pans 314 and 316 serve to retain the wedge sled and drivers within the cartridge body 302.

In various embodiments, the cartridge body 302 additionally has at least one release member formed thereon that protrudes in the proximal direction. In the embodiment depicted in FIG. 14, two release members 320 are formed on the proximal end 319 of the cartridge 300. The release members 320 each have a wedge shape that defines a sloped pivot surface 321 that are configured to pivotally support a portion of the anvil mounting portion 223 thereon.

Installation of a Staple Cartridge

An understanding of the operation of a anvil lockout system may be gleaned from reference to FIGS. 16-25. FIGS. 16 and 17 illustrate the position of the anvil 220 relative to the elongate channel 210 prior to installing a staple cartridge 300. When in that "unloaded" and open position, the anvil lock member 260 is biased in the distal direction by spring 269 such that the cam surfaces 263 on the anvil lock member 260 are in contact with the end surfaces 227, 229 of the trunnion walls 226, 228. The anvil lock member 260 pushes the anvil mounting portion 223 in the distal direction "DD" such that the trunnions 230 are seated in their respective locking notch 218. The cam surfaces 263 on the anvil lock member 260, in cooperation with the end wall surfaces 227, 229, also serve to pivot and retain the anvil in the open position as shown in FIGS. 16 and 17. As can be seen in FIG. 16, when in that position, the trunnion walls 226, 228 are supported on the rocker surfaces 248 on the pivot mount 240. When in that position, the surgeon cannot close the anvil 220 by actuating the closure trigger 152 to advance the distal closure tube 170. Because the closure tube segments cannot be advanced distally to close the anvil 220, the closure trigger 152 cannot be actuated to its fully closed position whereby the firing trigger 102 may be actuated. Thus, when no cartridge 300 is present, the end effector 200 may not be actuated.

FIGS. 18 and 19 illustrate the initial insertion of the staple cartridge 300 into the elongate channel 210. FIGS. 20 and 21 illustrate the end effector 200 after the staple cartridge 300 has been fully seated in the elongate channel 210. As can be seen in FIG. 20 for example, when the cartridge 300 has been fully seated, the release members 320 on the cartridge 300 engage the trunnion walls 226, 228 and serve to move the anvil mounting portion 223 in a proximal direction "PD" such that the trunnion walls 226, 228 now pivotally rest on the release members 320. As can be seen in FIG. 21, when in that position, the anvil mounting portion 223 has moved proximally such that the trunnions 230 are moved out of their respective locking notches 218 and into the bottom of the arcuate slot segment 216 into an "actuatable" position whereby the anvil 220 may be pivoted closed by actuating the closure trigger 152.

When the device 10 is in the starting position and the staple cartridge 300 has been loaded into the elongate channel as described above, both of the triggers 152, 102 are forward and the anvil 220 has been moved to the actuatable position, such as would be typical after inserting the loaded end effector 200 through a trocar or other opening into a body cavity. The instrument 10 is then manipulated by the clinician such that tissue "T" to be stapled and severed is positioned between the staple cartridge 300 and the anvil 200, as depicted in FIGS. 22 and 23. As discussed above, movement of the closure trigger 152 toward the pistol grip 24 causes the proximal closure tube segment 151, the flex neck assembly 70 and the distal closure tube segment 170 to move distally. As the distal closure tube segment 170 moves distally, it contacts a closure ledge 221 on the anvil 220. Pressure from the tissue captured between the anvil 220 and the staple cartridge 300 serves to move the anvil 220 such that the trunnions 230 are positioned to move within the arcuate trunnion slot segments 216. The surgeon may pivot the anvil 220 relative to the staple cartridge 300 to manipulate and capture the desired tissue "T" in the end effector 200. As the distal closure tube segment 170 contacts the closure ledge 221, the anvil 220 is pivoted towards a clamped position. The retracted knife bar 130 does not impede the selective opening and closing of the anvil 220.

Once the desired tissue "T" has been positioned between the anvil 220 and the cartridge 300, the clinician moves the closure trigger 152 proximally until positioned directly adjacent to the pistol grip 24, locking the handle 20 into the closed and clamped position. As can be seen in FIG. 25, when in the fully clamped position, the anvil trunnions 230 are located in the upper end of the arcuate slot portion 216 and the anvil tab 224 is received within the opening 176 in the distal closure tube segment 170. After tissue clamping has occurred, the clinician moves the firing trigger 102 proximally causing the knife bar 130 to move distally into the end effector 200. In particular, the knife bar 130 moves through the slot 236 in the pivot tab portion 234 of the anvil 220 and into the slot 304 in the cartridge body 302 to contact the wedge sled operably positioned within the staple cartridge 300. As the knife bar 130 is driven distally, it cuts the tissue T and drives the wedge sled distally which causes the staples to be sequentially fired into forming contact with the staple-forming undersurface 222 of the anvil 220. The clinician continues moving the firing trigger 102 until brought proximal to the closure trigger 152 and pistol grip 24. Thereby, all of the ends of the staples are bent over as a result of their engagement with the anvil 220. The cutting edge 132 has traversed completely through the tissue T. The process is complete by releasing the firing trigger 102 and by then depressing the release button 120 while simultaneously squeezing the closure trigger 152. Such action results in the movement of the distal closure tube segment 170 in the proximal direction "D". As the anvil tab 224 is engaged by the opening 176 in the distal closure tube segment 170 it causes the anvil to pivot open. The end surfaces 227, 229 again contact the pusher surfaces 263 on the anvil lock member 260 to pivot the anvil to the open position shown in FIGS. 20 and 21 to enable the spent cartridge 300 to be removed from the elongate channel 210.

Figure 26:
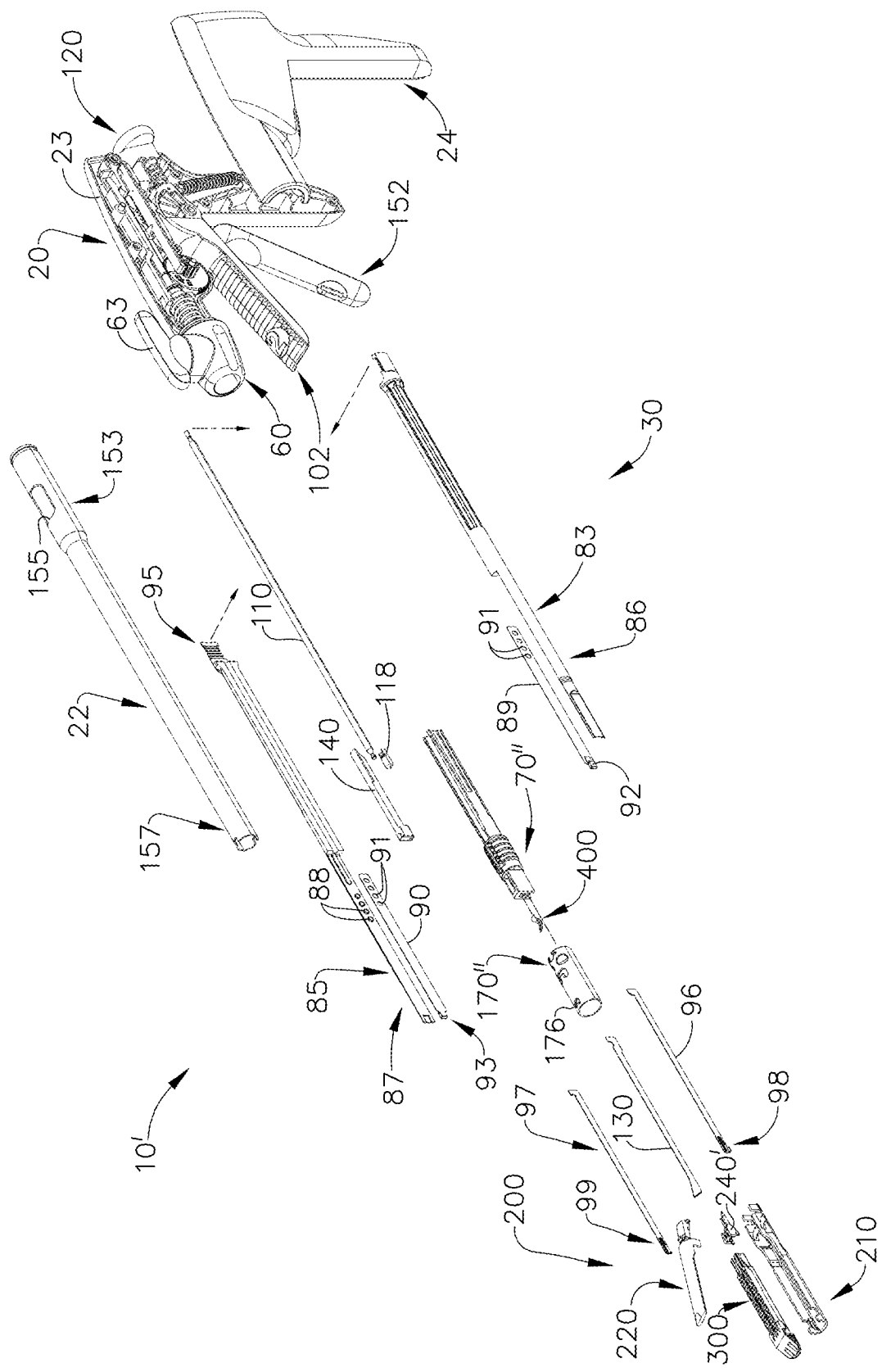
FIG. 26 is an exploded assembly view of another surgical stapling instrument embodiment.
Figure 28:
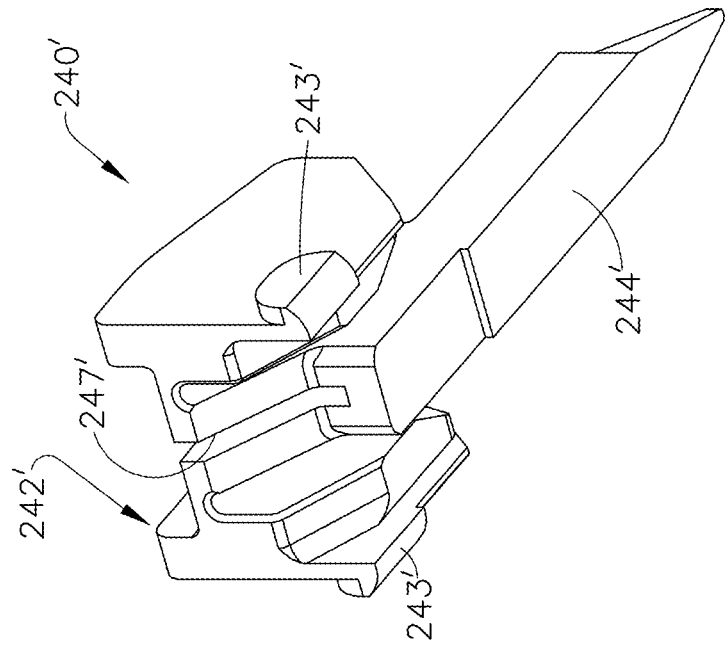
FIG. 28 is a bottom perspective view of the pivot mount embodiment of FIG. 27.
Figure 27:
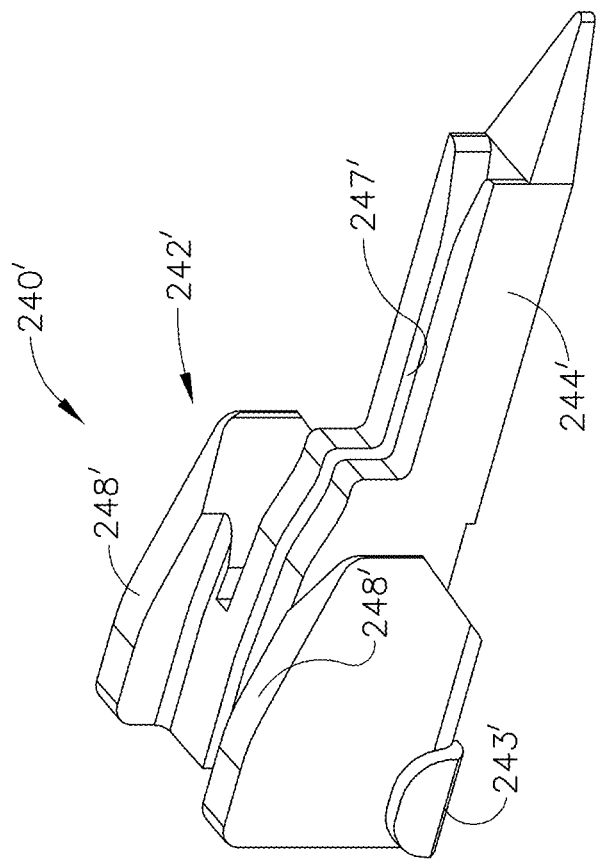
FIG. 27 is a perspective view of another pivot mount embodiment.

FIGS. 26-42 illustrate an alternative surgical stapling instrument 10' that is similar in construction and operation to surgical stapling instrument 10 except for the differences discussed below. This embodiment, for example, employs the pivot mount 240' illustrated in FIGS. 29 and 30. As can be seen in FIGS. 27 and 28 one form of a pivot mount 240' has a body portion 242' that is configured to be attached to the elongate channel 210. For example, the body portion 242' may be formed with two opposed attachment tabs 243' that are configured to retainingly engage tab openings 211 (FIG. 26) formed in the elongate channel 210. In addition, the pivot mount 240' has a proximally extending foot portion 244' that has a slot 247' extending therethrough for axially receiving the knife bar 130. Various embodiments of the pivot mount 240' further include rocker surfaces 248' formed on the body portion 242' for pivotally receiving the trunnion walls 226, 228 of the anvil 220 thereon.

This embodiment also includes an anvil lockout system 250' that prevents closure of the anvil 220 when a staple cartridge 300' has not been properly installed in the elongate channel 210. Referring to FIGS. 29 and 30, for example, an embodiment of an anvil lockout system 250' includes an anvil lock member 400 that is configured to contact the anvil mounting portion 223 as will be discussed in further detail below. In at least one form, the anvil lock member 400 comprises a leaf spring 402 that has a slot 404 therein for accommodating the knife bar 130. The leaf spring 402 is configured for attachment to the channel guide 79" of the flex neck assembly 70".

Figure 31:
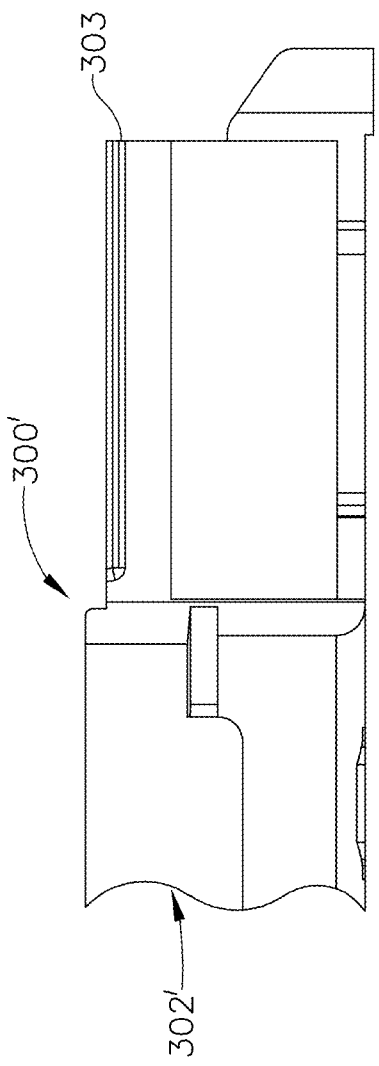
FIG. 31 is a partial side elevational view of a proximal end portion of another surgical staple cartridge embodiment.
Figure 32:
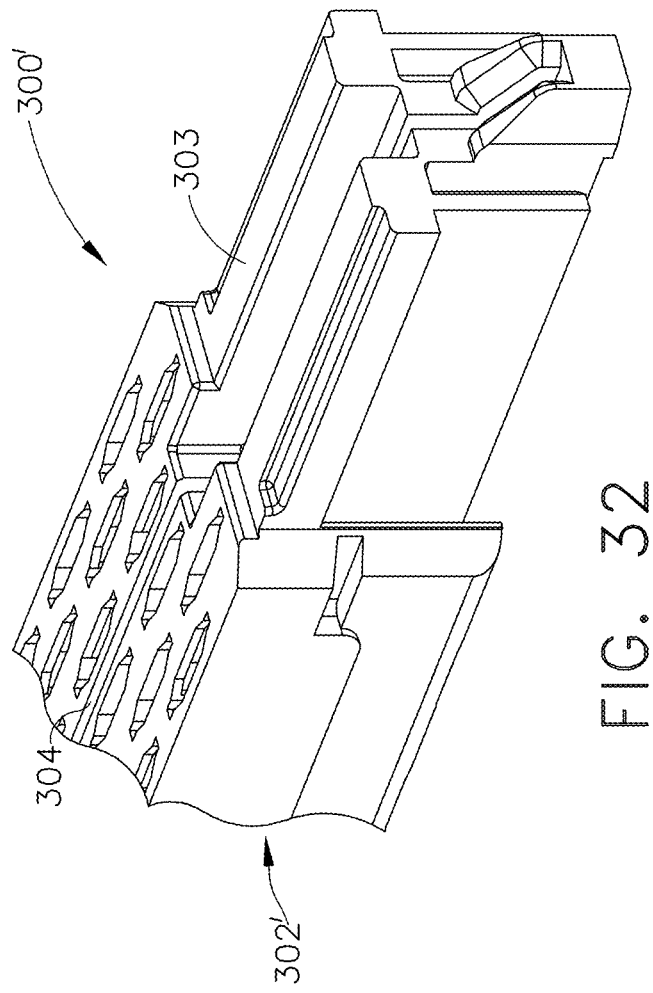
FIG. 32 is a perspective view of a proximal end portion of the surgical staple cartridge embodiment of FIG. 31.

As can be seen in FIGS. 31 and 32, in at least one form, the surgical staple cartridge 300' includes a cartridge body 302' that is similar to the surgical staple cartridge 300 described above, except for the differences discussed below. FIG. 29 depicts a wedge sled 360 that is supported within the cartridge body 302' in the manner described above. In this embodiment, the proximal end portion 303 of the cartridge body 302' is configured to contact a portion of the anvil mounting portion 223 and urge the anvil 220 proximally when the cartridge body 302' is seated within the elongate channel 210.

Figure 33:
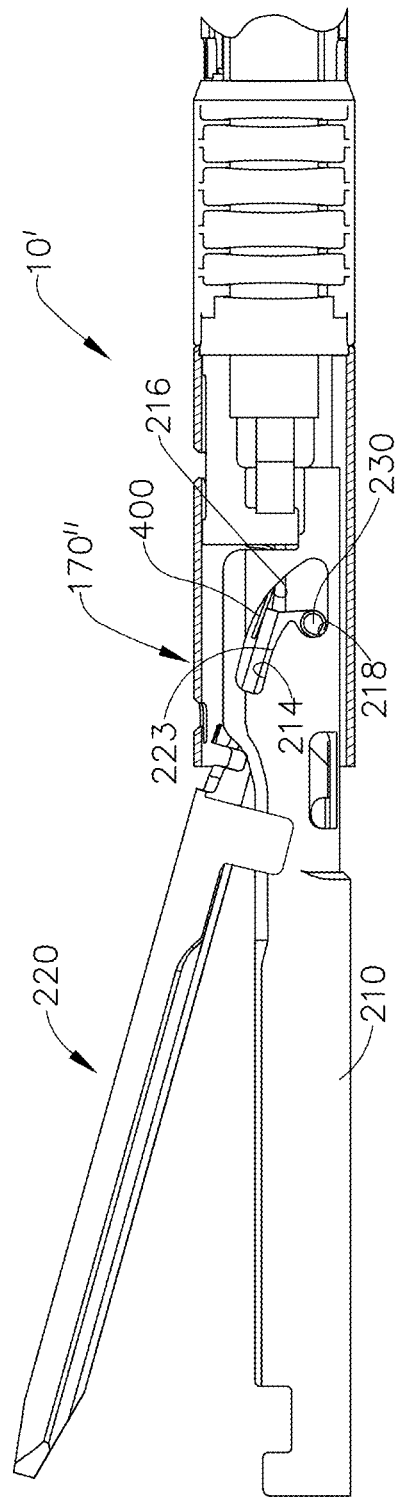
FIG. 33 is a side view of another end effector embodiment prior to seating a staple cartridge in the elongate channel.
Figure 34:
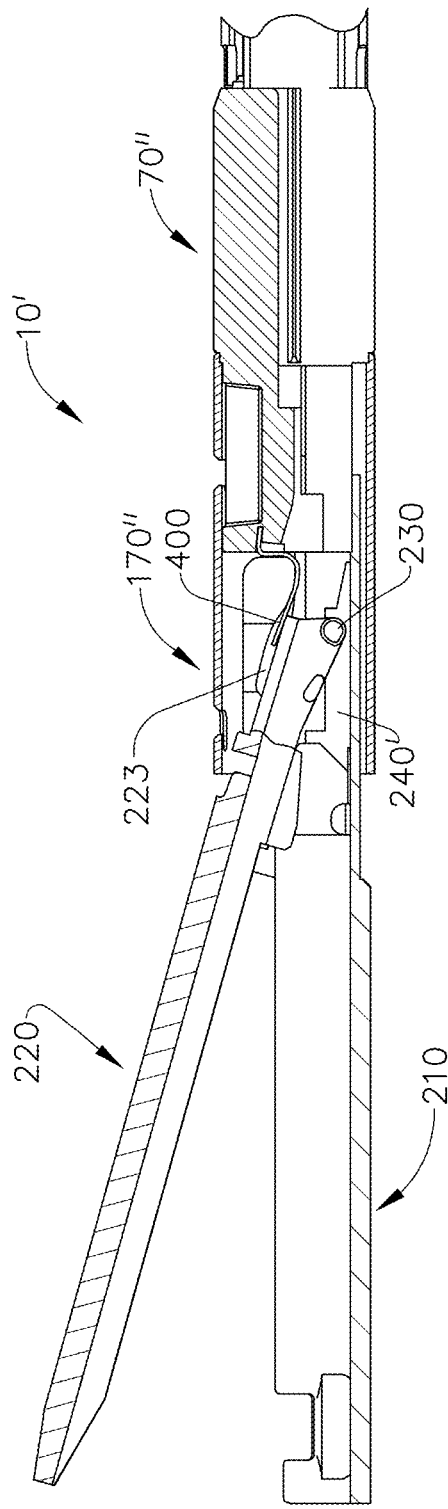
FIG. 34 is a cross-sectional view of the end effector depicted in FIG. 33.

An understanding of the operation of a anvil lockout system 250' may be gleaned from reference to FIGS. 33-42. FIGS. 33 and 34 illustrate the position of the anvil 220 relative to the elongate channel 210 prior to installing a staple cartridge 300'. When in that "unloaded" position, the anvil lock member 400 has engaged the upper surface of the anvil support portion 223 such that the anvil 220 is pivoted to the open position on the rocker surfaces 248' on the pivot mount 140'. When in that position, the trunnions 230 are seated in their respective locking notch 218. When in that position, the surgeon cannot close the anvil 220 by actuating the closure trigger 152 to advance the distal closure tube 170'. Because the closure tube segments cannot be advanced distally to close the anvil 220, the closure trigger 152 cannot be actuated to its fully closed position whereby the firing trigger 102 may be actuated. Thus, when no cartridge 300' is present, the end effector 200 may not be actuated.

FIGS. 35 and 36 illustrate the initial insertion of the staple cartridge 300' into the elongate channel 210. FIGS. 37 and 38 illustrate the end effector 200 after the staple cartridge 300' has been fully seated in the elongate channel 210. As can be seen in FIG. 37 for example, when the cartridge 300' has been fully seated, the proximal end portion 303 on the cartridge 300' engages the trunnion walls 226, 228 and serves to move the anvil mounting portion 223 in a proximal direction "PD" such that the trunnions are moved out of their respective locking notch 218 and into an actuatable position the bottom of the arcuate slot segment 216. The anvil 220 is now in position to be pivoted closed by actuating the closure trigger 152.

Figure 39:
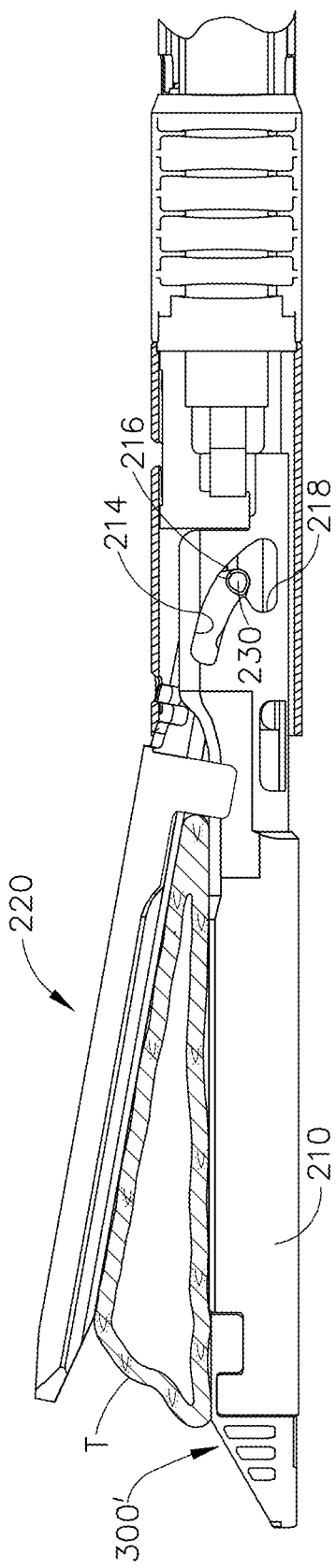
FIG. 39 is a side elevational view of the end effector of FIGS. 33-38 clamping tissue.
Figure 40:
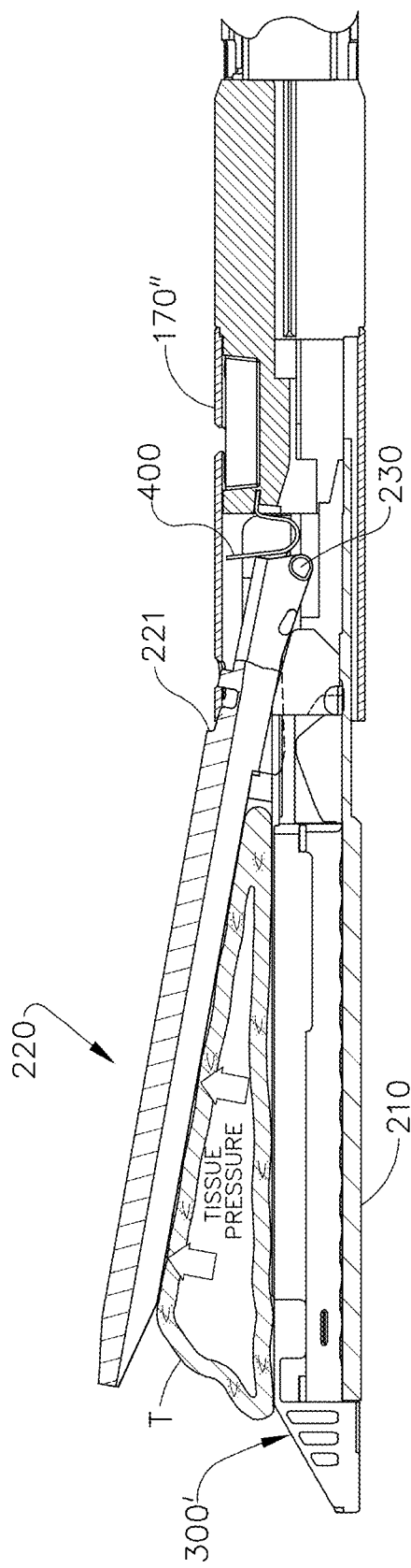
FIG. 40 is a cross-sectional view of the end effector of FIG. 39.

When the device 10' is in the starting position and the staple cartridge 300' has been loaded into the elongate channel 210 as described above, both of the triggers 152, 102 are forward and the anvil 220 is open and in the actuatable position, such as would be typical after inserting the loaded end effector 200 through a trocar or other opening into a body cavity. The instrument 10' is then manipulated by the clinician such that tissue "T" to be stapled and severed is positioned between the staple cartridge 300' and the anvil 220, as depicted in FIGS. 39 and 40. As discussed above, movement of the closure trigger 152 toward the pistol grip 24 causes the proximal closure tube segment 151, the flex neck assembly 70" and the distal closure tube segment 170" to move distally. As the distal closure tube segment 170' moves distally, it contacts a closure ledge 221 on the anvil 220. Pressure from the tissue captured between the anvil 220 and the staple cartridge 300' serves to move the anvil 220 such that the trunnions 230 are positioned to move within the arcuate trunnion slot segments 216. The surgeon may pivot the anvil 220 relative to the staple cartridge to manipulate and capture the desired tissue "T" in the end effector 200. As the distal closure tube segment 170" contacts the closure ledge 221, the anvil 220 is pivoted towards a clamped position. The retracted knife bar 130 does not impede the selective opening and closing of the anvil 220.

Once the desired tissue "T" has been positioned between the anvil 220 and the cartridge 300', the clinician moves the closure trigger 152 proximally until positioned directly adjacent to the pistol grip 24, locking the handle 20 into the closed and clamped position. As can be seen in FIG. 42, when in the fully clamped position, the anvil trunnions 230 are located in the upper end of the arcuate slot portion 216 and the anvil tab 224 is received within the opening 176 in the distal closure tube segment 170". After tissue clamping has occurred, the clinician moves the firing trigger 102 proximally causing the knife bar 130 to move distally into the end effector 200. In particular, the knife bar 130 moves through the slot 236 in the pivot tab portion 234 of the anvil 220 and into the slot 304 in the cartridge body 302' to contact the wedge sled 360 operably positioned in therein. As the knife bar 130 is driven distally, it cuts the tissue T and drives the wedge sled 360 distally which causes the staples to be sequentially fired into forming contact with the staple-forming undersurface 222 of the anvil 220. The clinician continues moving the firing trigger 102 until brought proximal to the closure trigger 152 and pistol grip 24. Thereby, all of the ends of the staples are bent over as a result of their engagement with the anvil 220. The cutting edge 132 has traversed completely through the tissue T. The process is complete by releasing the firing trigger 102 and by then depressing the release button 120 while simultaneously squeezing the closure trigger 152. Such action results in the movement of the distal closure tube segment 170" in the proximal direction "D". As the anvil tab 224 is engaged by the opening 176 in the distal closure tube segment 170", it causes the anvil 220 to pivot open. The anvil lock member 400 applies a biasing force to the upper surface of the trunnion walls of the anvil mounting portion 223 and serves to pivot the anvil to the open position shown in FIGS. 33 and 34 to enable the spent cartridge 300' to be removed from the elongate channel 210.

The various unique and novel features of the above-described embodiments serve to prevent the end effector from being closed when a surgical staple cartridge is not present or has not been properly seated within the elongate channel. When the anvil is in the locked position wherein the anvil trunnions are retained in their respective locking notches, the anvil is retained in the open position. When in the open position, the end effector cannot be inadvertently inserted through a trocar. Because a full closure stroke is prevented, the firing system cannot be actuated. Thus, even if the clinician attempts to actuate the firing trigger, the device will not fire. Various embodiments also provide the clinician with feedback indicating that a cartridge is either not present or has not been properly installed in the elongate channel.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapling instrument comprising:
   (a) a shaft extending along a longitudinal axis to a distal end; and
   (b) an end effector operatively coupled with the shaft, wherein the end effector includes:
      (i) a first jaw including:
         (A) an anvil,
         (B) at least one trunnion, and
         (C) at least one first abutment surface, and
      (ii) a second jaw configured to cooperate with the first jaw to clamp tissue, wherein the second jaw is configured to support a stapling assembly, wherein the second jaw includes:
         (A) at least one locking notch configured to receive the at least one trunnion, and
         (B) at least one second abutment surface configured to engage the at least one first abutment surface when the at least one trunnion is received within the at least one locking notch to thereby prevent closure of the first jaw toward the second jaw.

2. The surgical stapling instrument of claim 1, wherein the first jaw includes at least one trunnion wall, wherein the at least one trunnion protrudes from the at least one trunnion wall, wherein the at least one trunnion wall includes the at least one first abutment surface.

3. The surgical stapling instrument of claim 1, wherein the second jaw includes a pivot mount, wherein the pivot mount includes the at least one second abutment surface.

4. The surgical stapling instrument of claim 3, wherein the pivot mount includes an upstanding central portion having a slot extending therethrough for axially receiving a knife bar.

5. The surgical stapling instrument of claim 4, wherein the at least one second abutment surface includes a pair of second abutment surfaces positioned on opposite sides of the central portion.

6. The surgical stapling instrument of claim 3, wherein the second jaw includes an elongate channel configured to receive the stapling assembly, wherein the pivot mount is attached to the elongate channel.

7. The surgical stapling instrument of claim 6, wherein the pivot mount includes at least one attachment tab, wherein the elongate channel includes at least one opening configured to receive the at least one attachment tab.

8. The surgical stapling instrument of claim 6, wherein the pivot mount includes a retainer lug, wherein the elongate channel includes at least one opening configured to receive the retainer lug.

9. The surgical stapling instrument of claim 1, wherein the at least one locking notch is configured to receive the at least one trunnion when the stapling assembly is not supported by the second jaw.

10. The surgical stapling instrument of claim 1, wherein the second jaw includes at least one trunnion slot, wherein the at least one trunnion slot includes the at least one locking notch and at least one arcuate slot segment configured to receive the at least one trunnion.

11. The surgical stapling instrument of claim 10, wherein the at least one first abutment surface is configured to disengage the at least one second abutment surface when the at least one trunnion is received within the at least one arcuate slot segment to thereby permit closure of the first jaw toward the second jaw.

12. The surgical stapling instrument of claim 10, wherein the at least one trunnion is configured to move into the at least one arcuate slot segment in response to the stapling assembly being supported by the second jaw.

13. The surgical stapling instrument of claim 1, wherein the at least one first abutment surface tapers downwardly in a proximal direction.

14. The surgical stapling instrument of claim 1, wherein the at least one second abutment surface tapers downwardly in a proximal direction.

15. The surgical stapling instrument of claim 1, wherein the at least one trunnion is resiliently biased toward the at least one locking notch.

16. A surgical stapling instrument comprising:
  (a) a shaft extending along a longitudinal axis to a distal end; and
  (b) an end effector operatively coupled with the shaft, wherein the end effector includes:
    (i) a first jaw including:
      (A) an anvil,
      (B) at least one trunnion wall, and
      (C) at least one trunnion protruding from the at least one trunnion wall, and
    (ii) a second jaw configured to cooperate with the first jaw to clamp tissue, wherein the second jaw is configured to support a stapling assembly, wherein the second jaw includes:
      (A) at least one locking notch configured to receive the at least one trunnion, and
      (B) at least one rocker surface configured to engage the at least one trunnion wall when the at least one trunnion is received within the at least one locking notch to thereby prevent closure of the first jaw toward the second jaw.

17. The surgical stapling instrument of claim 16, wherein the second jaw includes at least one trunnion slot, wherein the at least one trunnion slot includes the at least one locking notch and at least one arcuate slot segment configured to receive the at least one trunnion, wherein the at least one trunnion wall is configured to disengage the at least one rocker surface when the at least one trunnion is received within the at least one arcuate slot segment to thereby permit closure of the first jaw toward the second jaw.

18. The surgical stapling instrument of claim 17, wherein the at least one locking notch is configured to receive the at least one trunnion when the stapling assembly is not supported by the second jaw, wherein the at least one trunnion is configured to move into the at least one arcuate slot segment in response to the stapling assembly being supported by the second jaw.

19. The surgical stapling instrument of claim 16, wherein the at least one rocker surface tapers downwardly in a proximal direction.

20. A surgical stapling instrument comprising:
  (a) a shaft extending along a longitudinal axis to a distal end; and
  (b) an end effector operatively coupled with the shaft, wherein the end effector includes:
    (i) a first jaw including:
      (A) an anvil,
      (B) at least one trunnion wall, and
      (C) at least one trunnion protruding from the at least one trunnion wall, and
    (ii) a second jaw configured to cooperate with the first jaw to clamp tissue, wherein the second jaw is configured to support a stapling assembly, wherein the second jaw includes:
      (A) at least one locking notch configured to receive the at least one trunnion, and
      (B) a pivot block having at least one surface configured to engage the at least one trunnion wall when the at least one trunnion is received within the at least one locking notch to thereby prevent closure of the first jaw toward the second jaw.

\* \* \* \* \*